(12) United States Patent
Buettelmann et al.

(10) Patent No.: US 7,005,432 B2
(45) Date of Patent: Feb. 28, 2006

(54) SUBSTITUTED IMIDAZOL-PYRIDAZINE DERIVATIVES

(75) Inventors: Bernd Buettelmann, Schopfheim (DE); Marie-Paule Heitz Neidhart, Hagenthal le Bas (FR); Georg Jaeschke, Basel (CH); Emmanuel Pinard, Linsdorf (FR)

(73) Assignee: Hoffman-La Roche Inc., Nutley, NJ (US)

( * ) Notice: Subject to any disclaimer, the term of this patent is extended or adjusted under 35 U.S.C. 154(b) by 91 days.

(21) Appl. No.: 10/434,955

(22) Filed: May 9, 2003

(65) Prior Publication Data

US 2003/0229096 A1 Dec. 11, 2003

(30) Foreign Application Priority Data

May 16, 2002 (EP) ............................................. 02010217

(51) Int. Cl.
*A61K 31/501* (2006.01)
*C07D 403/06* (2006.01)

(52) U.S. Cl. ................................... 514/252.05; 544/238
(58) Field of Classification Search ................ 544/238; 514/252.05
See application file for complete search history.

(56) References Cited

U.S. PATENT DOCUMENTS

| | | | |
|---|---|---|---|
| 5,962,472 A | 10/1999 | Bourson et al. | |
| 6,265,426 B1 | 7/2001 | Alanine et al. | |
| 6,310,213 B1 | 10/2001 | Alanine et al. | |
| 6,339,093 B1 | 1/2002 | Alanine et al. | |
| 6,359,138 B1 | 3/2002 | Alanine et al. | |
| 2001/0047014 A1 | 11/2001 | Alanine et al. | |
| 2001/0047031 A1 | 11/2001 | Alanine et al. | |

FOREIGN PATENT DOCUMENTS

| | | |
|---|---|---|
| EP | 0 937 458 | 8/1999 |
| EP | 1 254 661 | 4/2002 |
| WO | WO 02/28814 | 4/2002 |
| WO | WO 02/085352 | 10/2002 |
| WO | 03/097637 | * 11/2003 |

OTHER PUBLICATIONS

Robert McBurney, Therapeutic Potential of NMDA Antagonists in Neurodegenerative Diseases, Nuerobiology of Aging, vol. 15, No. 2, pp. 271–273 (1994).*
Ikonomidou et al., Neurodegenerative Disorders: Clues from Glutamate and Energy Metabolism, Critical Reviews in Neurobiology, 10(2), pp. 239–263 (1996).*
Bryant et al., *J. Heterocycl. Chem.*, vol. 32(5), pp. 1473–1476 (1995).
M. Adamczyk et al., *J. Org. Chem.*, vol. 49, pp. 4226–4237 (1984).
J. S. Sawyer et al., *J. Am. Chem. Soc.*, vol. 110, pp. 842–853 (1988).

* cited by examiner

*Primary Examiner*—Johann Richter
*Assistant Examiner*—Ebenezer Sackey
(74) *Attorney, Agent, or Firm*—George W. Johnston; Patricia S. Rocha-Tramaloni; Kimberly J. Prior

(57) ABSTRACT

The present invention relates to compounds of formula

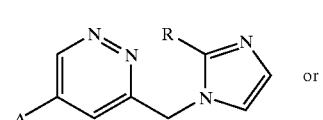

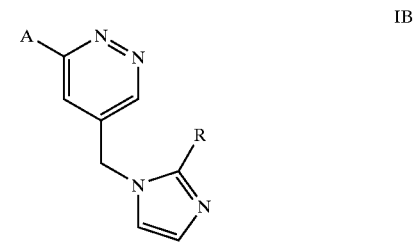

wherein A is an unsubstituted or substituted cyclic group; and
R is hydrogen or lower alkyl;
or a pharmaceutically acceptable acid addition salt thereof.

These compounds are NMDA NR-2B receptor subtype specific blockers and are useful in the treatment of neurodegeneration, depression and pain.

22 Claims, No Drawings

SUBSTITUTED IMIDAZOL-PYRIDAZINE DERIVATIVES

SUMMARY OF THE INVENTION

The present invention relates to substituted imidazol-pyridazine derivatives that are N-methyl-D-aspartate-receptor subtype selective blockers useful in the therapy of CNS disorders. The invention also relates to pharmaceutical compositions including, and methods of treatment using, these novel compounds. The invention also relates to methods of preparing these compounds.

BACKGROUND

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Possible therapeutic indications for NMDA NR-2B receptor subtype specific blockers include acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis) and neurodegeneration associated with bacterial or viral infections, and, in addition, depression and chronic and acute pain.

Furthermore, EP 1254661 describes a method for preventing dyskinesias with selective NMDA antagonists and WO 0285352 discloses the usefulness of NMDA modulators for the treatment of addictive illnesses, such as smoking cessation.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain alkyl group containing from 1 to 7 carbon atoms, for example, methyl, ethyl, propyl, isopropyl, butyl and the like. Preferred lower alkyl groups contain from 1 to 4 carbon atoms.

The term "halogen" denotes chlorine, iodine, fluorine and bromine.

The term "lower alkoxy" denotes a group wherein the alkyl residue is as defined above and the alkyl group is connected via an oxygen atom.

The term "cycloalkyl" denotes a carbon ring with 3 to 6 carbon atoms, preferred is cyclopropyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

In one embodiment, the present invention relates to compounds of the formula

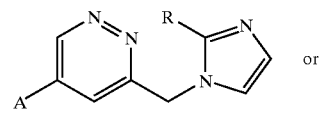

or

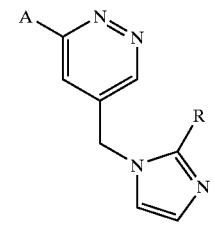

wherein

A is an unsubstituted or substituted cyclic group; and

R is hydrogen or lower alkyl;

or a pharmaceutically acceptable acid addition salt thereof.

The compounds of formula I and their pharmaceutically acceptable salts have valuable therapeutic properties. Specifically these compounds are NMDA(N-methyl-D-aspartate)-receptor subtype selective blockers that have a key function in modulating neuronal activity and plasticity, making them important participants in mediating processes underlying development of CNS, as well as learning and memory formation.

In a preferred embodiment of the invention, cyclic group A in formula I is selected from:

a)

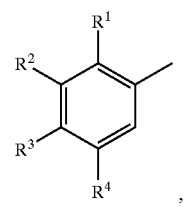

b)

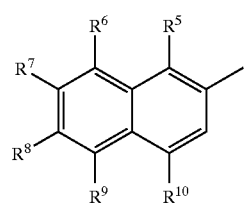

c)

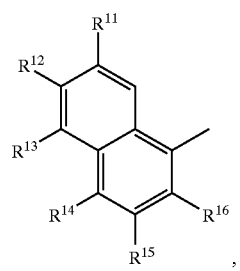

-continued d) 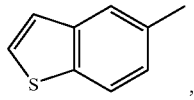, e) 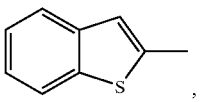, f) 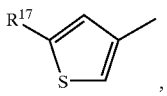, g) 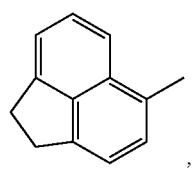, h) 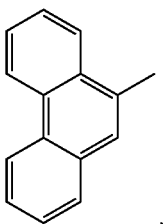, i) 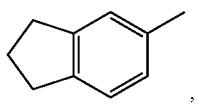, j) 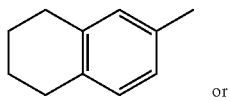 or k) 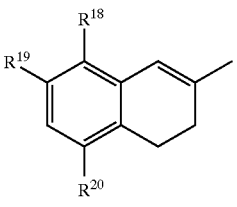, wherein
  $R^1$–$R^4$ are each independently selected from hydrogen, halogen, $CF_3$, $CHF_2$, $C(CH_3)F_2$, $C_3$–$C_6$-cycloalkyl, lower alkoxy, lower alkyl, $OCF_3$ and phenyl;
  $R^5$–$R^{10}$ are each independently selected from hydrogen, halogen, lower alkyl, lower alkoxy and $CHF_2$;
  $R^{11}$–$R^{16}$ are each independently selected from hydrogen, halogen, lower alkoxy and lower alkyl;
  $R^{17}$ is hydrogen or $CHF_2$; and
  $R^{18}$–$R^{20}$ are each independently selected from hydrogen, lower alkyl and lower alkoxy.

The following types of compounds are encompassed by formula I:

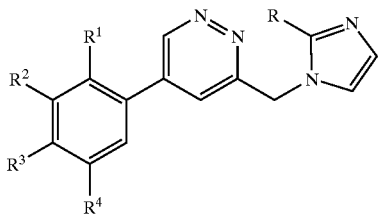
IA1

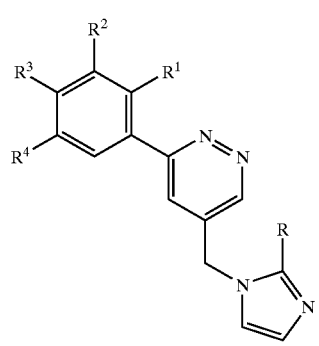
IB1

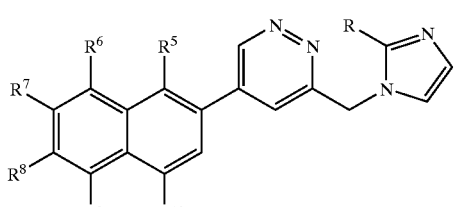
IA2

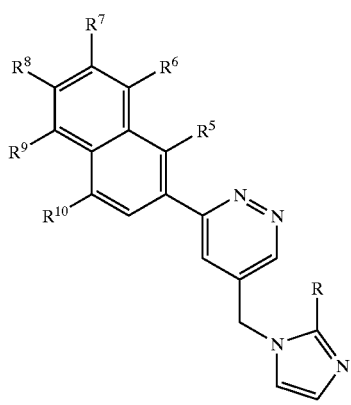
IB2

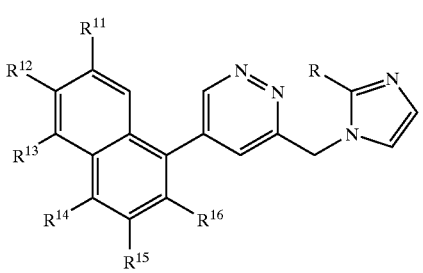
IA3

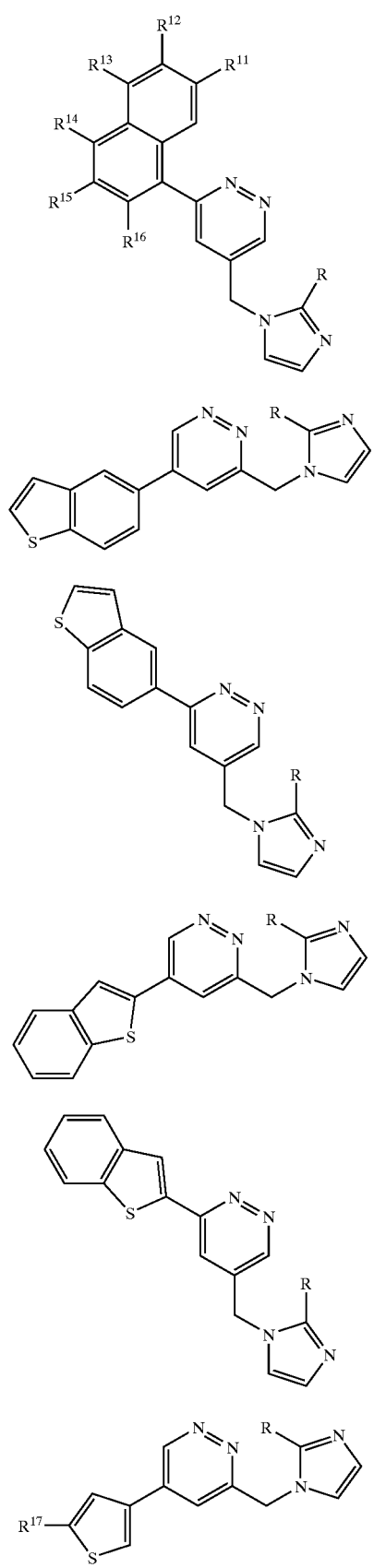
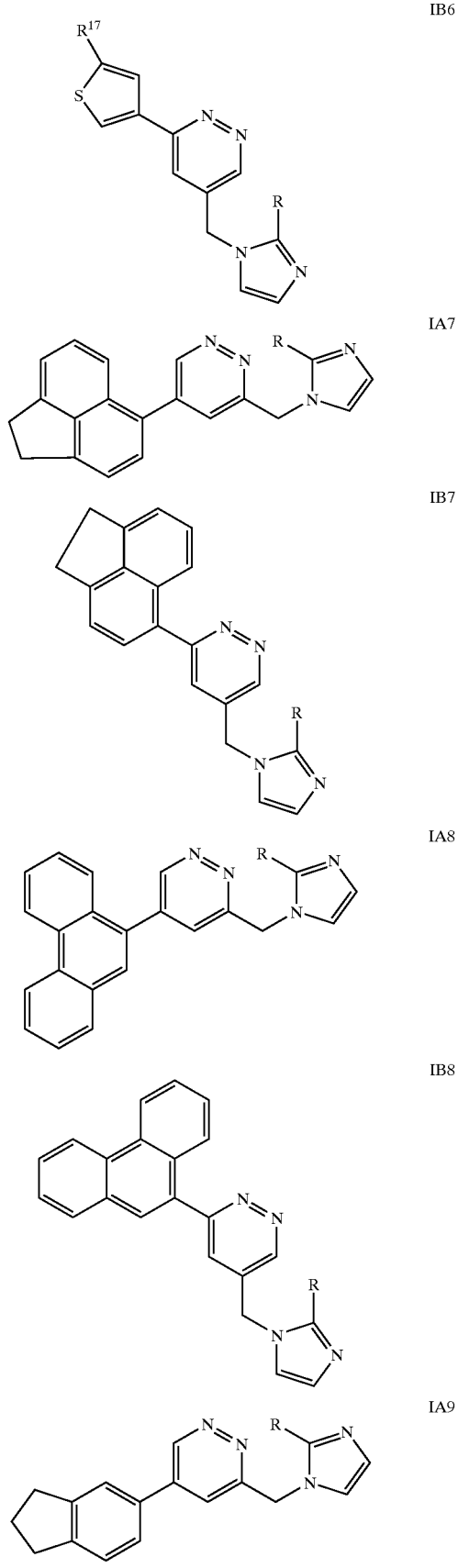

-continued

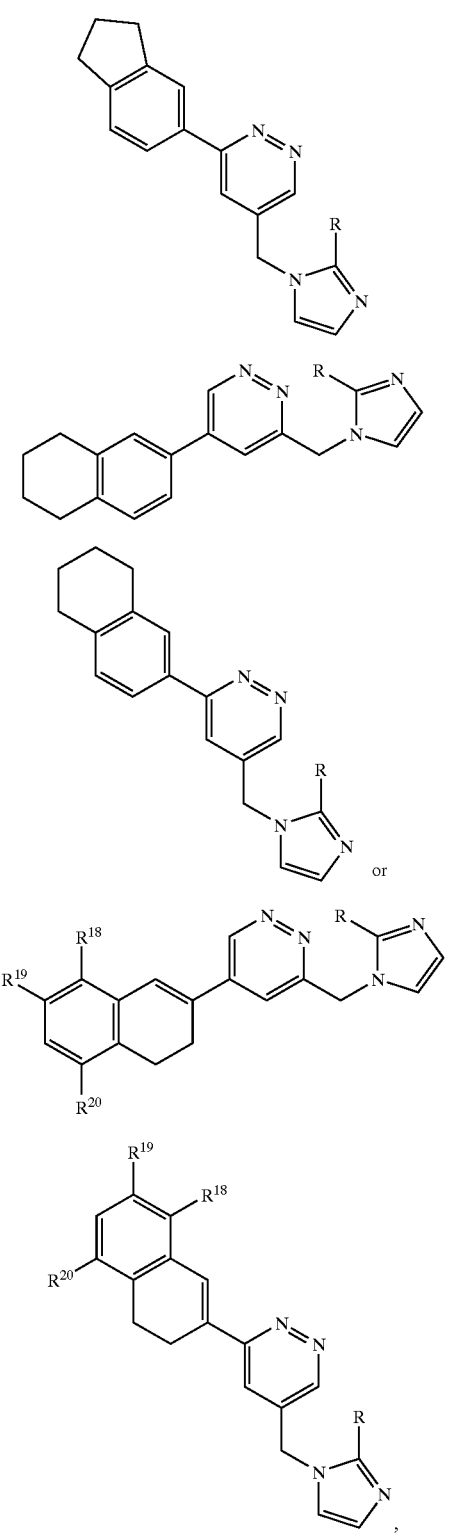

wherein R¹–R²⁰ are as defined above.

Compounds of formulas IA1, IA2, IA3, IA4, IA5, IA6, IA7, IA8, IA9, IA10 and IA11 are particularly preferred.

Preferred compounds of the present invention are those, wherein A in formula I is the group a) defined above.

Specific preferred compounds, which fall under this group are the followings:

5-(3-chloro-4-fluoro-phenyl)-3-(2-methyl-imidazol-1-yl-methyl)-pyridazine,
3-(2-methyl-imidazol-1-yl-methyl)-5-(3-trifluoromethyl-phenyl)-pyridazine,
5-(3-difluoromethyl-4-fluoro-phenyl)-3-(2-methyl-imidazol-1-yl-methyl)-pyridazine,
5-[3-(1,1-difluoro-ethyl)-phenyl]-3-(2-methyl-imidazol-1-yl-methyl)-pyridazine,
5-[3-(1,1-difluoro-ethyl)-4-fluoro-phenyl]-3-(2-methyl-imidazol-1-yl-methyl)-pyridazine,
5-[3-(1,1-difluoro-ethyl)-4-fluoro-phenyl]-3-(2-methyl-imidazol-1-yl-methyl)-pyridazine,
5-(4-fluoro-3-methyl-phenyl)-3-(2-methyl-imidazol-1-yl-methyl)-pyridazine,
5-(4-chloro-3-methyl-phenyl)-3-(2-methyl-imidazol-1-yl-methyl)-pyridazine,
5-[3-(1,1-difluoro-ethyl)-5-fluoro-phenyl]-3-(2-methyl-imidazol-1-yl-methyl)-pyridazine,
5-(3-difluoromethyl-4-fluoro-phenyl)-3-(2-ethyl-imidazol-1-ylethyl)-pyridazine or
5-(3-cyclopropyl-4-fluoro-phenyl)-3-(2-methyl-imidazol-1-yl-methyl)-pyridazine.

Also preferred are compounds of formula I, wherein A is the group d), for example, the compound
5-benzo[b]thiophen-5-yl-3-(2-methyl-imidazol-1-yl-methyl)-pyridazine.

A further preferred group of compounds are those, wherein A is the group k), for example, the compound
5-(3,4-dihydro-naphthalen-2-yl)-3-(2-methyl-imidazol-1-yl-methyl)-pyridazine.

The afore-mentioned compounds of formula I can be prepared in accordance with the invention by
a) reacting a compound of formula

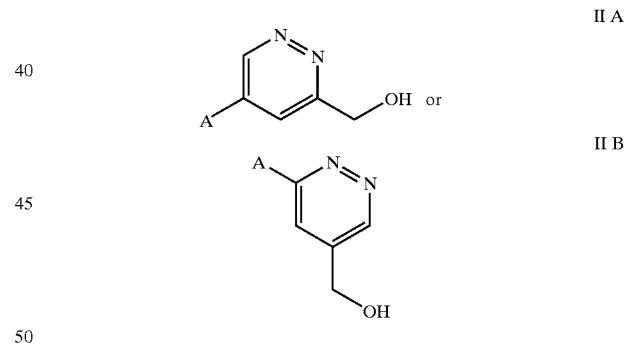

with a compound of formula

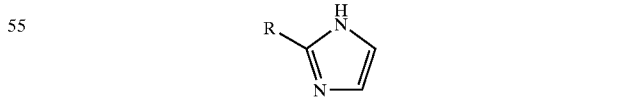

to give a compound of formula

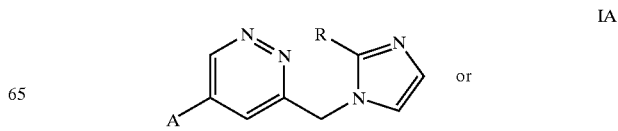

-continued

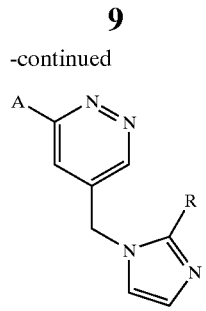

IB wherein A is the group a), b), c), d), e), f), g), h), i), j) or k) as described above and R is hydrogen or lower alkyl, or b) reacting a compound of formula

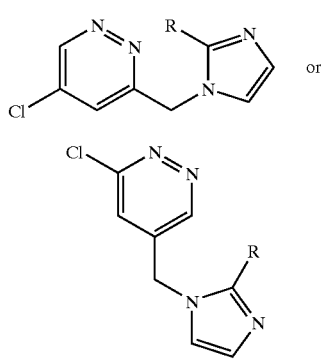

IV A or

IV B with a compound of formula

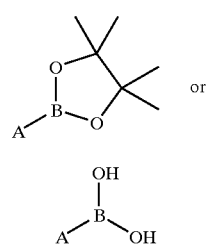

V or

VI to obtain a compound of formula

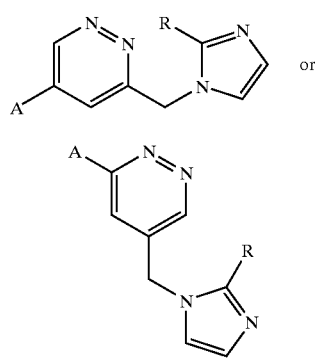

IA or

IB wherein A is the group a), b), c), d), e), f), g), h), i), j) or k) as described above and R is hydrogen or lower alkyl, and if desired, converting the compound of formula I obtained into a pharmaceutically acceptable salt.

In the following the preparation of compounds of formulas IA and IB are described in more detail:

In accordance with the process variants, described above, and with schemes 1–5, described below, compounds of formula IA and IB may be prepared by known procedures, for example the following:

In the following schemes 1–5 are described processes for preparation of compounds of formula IA, starting from known compounds, from commercial products or from compounds, which can be prepared in conventional manner.

The preparation of compounds of formula IA and IB are further described in more detail in working examples 1–73 and in examples 74–180.

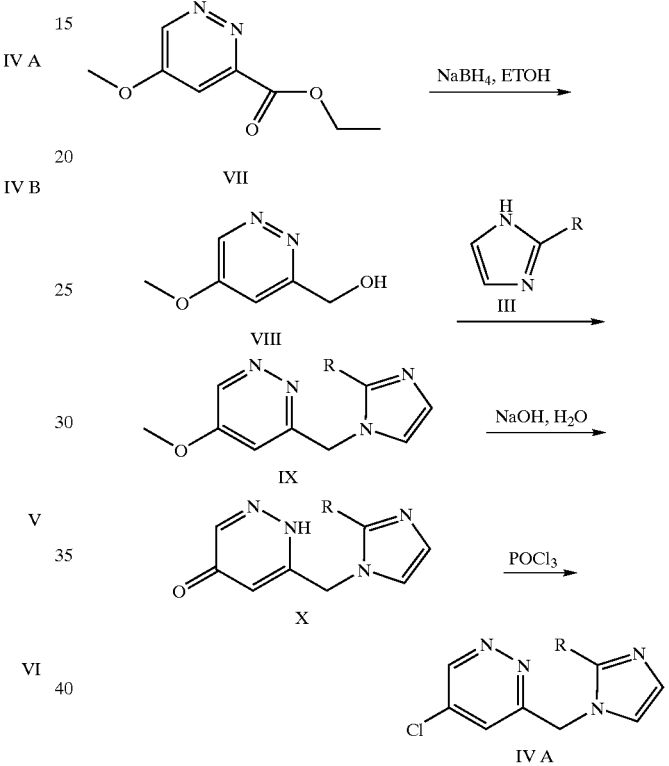

Scheme 1

Starting from 3-chloro-5-methoxy-pyridazine (Bryant, R. D.; Kunng, F.-A.; South, M. S. *J. Heterocycl. Chem.* (1995), 32(5), 1473–6.), the compound of formula VII may be prepared as follows: 3-Chloro-5-methoxy-pyridazine, bis (triphenylphosphine)palladium dichloride and triethyl amine in ethanol are heated at about 120° C. under a 40 bar pressure of carbon monoxide for about 5 hours. Reaction mixture is cooled, filtered and concentrated in vacuo. The residue is taken in $CH_2Cl_2$, washed with $H_2O$, dried over $Na_2SO_4$ and concentrated in vacuo to provide 5-methoxy-pyridazine-3-carboxylic acid ethyl ester (VII).

5-Methoxy-pyridazine-3-carboxylic acid ethyl ester is dissolved in ethanol under argon. Reaction mixture is cooled to 0° C. and treated with $NaBH_4$. After 10 minutes, reaction mixture is warmed to room temperature, stirred for about 1 hour and treated successively with HCl and saturated sodium bicarbonate to adjust the pH at 8. Solvent is removed in vacuo and the residue is stirred with MeOH. The suspension is filtered and the filtrate is concentrated.

The obtained (5-methoxy-pyridazin-3-yl)-methanol (VIII) is dissolved in $MeCl_2$ under argon and a drop of DMF is added. The mixture is cooled with an icebath, thionyl-chloride is added dropwise and the reaction mixture was allowed to warm to room temperature. After 30 minutes stirring, the orange solution was cooled to 0° C., and saturated NaHCO₃ solution is added dropwise. The aqueous layer is extracted with MeCl₂. The combined organic layers are dried over Na₂SO₄, filtered and concentrated in vacuo and treated with a appropriate imidazole (III). Reaction mixture is heated at about 100° C. for 2 hours then cooled to room temperature to provide the corresponding 5-methoxy-3-(imidazol-1-yl-methyl)-pyridazine (IX).

The 5-methoxy-3-(imidazol-1-yl-methyl)-pyridazine (IX) is dissolved in dioxane and NaOH is added. The mixture is refluxed for about 7 hours, cooled to room temperature and quenched with HCl. The pH is adjusted to 8 with saturated solution of NaHCO₃. The solvent is removed in vacuo and the residue is taken in MeOH. After filtration, the solvent is removed in vacuo and diluted with MeOH to provide the corresponding 6-(imidazol-1-yl-methyl)-1H-pyridazin-4-one (X).

6-(imidazol-1-yl-methyl)-1H-pyridazin-4-one (X) is taken in phosphorus oxychloride under argon. The mixture is stirred in a 60° C. oilbath for 1.5 hour. The solvent is removed in vacuo and the residue is dissolved in water under icebath cooling. The solution is neutralized with solid NaHCO₃ and the aqueous layer is extracted with MeCl₂ to provide the corresponding 5-chloro-3-(imidazol-1-yl-methyl)-pyridazine (IV A).

The compounds of formula IV B may be prepared in accordance with the above scheme, starting from

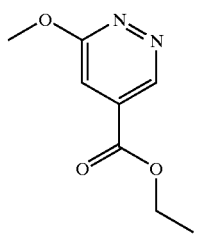

Scheme 2

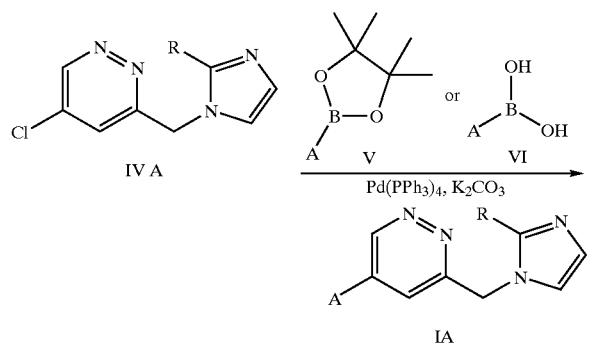

wherein A is the group a), b), c), d), e), f), g), h), i), j) or k) as described above and R is hydrogen or lower alkyl. Preferred compounds are those, wherein R is methyl.

In accordance with scheme 2, compounds of formula I may be prepared as follows: The corresponding 5-chloro-3-(imidazol-1-yl-methyl)-pyridazine (IV A), a corresponding boronic acid of formula VI or of a corresponding 4,4,5,5-tetramethyl-[1,3,2]-dioxaborolane (V), K₂CO₃ and tetrakis(triphenylphosphine)palladium are mixed and degassed dioxane is added. The mixture is refluxed for about 44 hours and the solvent is removed in vacuo. The residue is taken in MeCl₂, filtrated and the filtrate is concentrated in vacuo and a compound of formula IA is obtained.

In accordance with this scheme, a corresponding compound of formula IB may be obtained, using as starting material the compound of formula

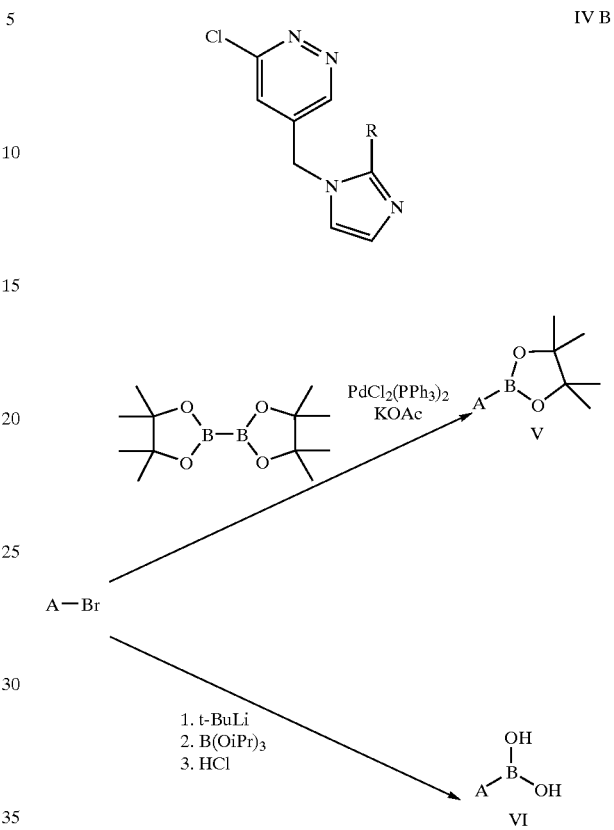

wherein A is the group a), b), c), d), e), f), g), h), i), j) or k) as described above.

A compound of formula A-Br may be prepared, for example as follows: 5-bromo-2-fluorobenzaldehyde in CH₂Cl₂ is treated at 0° C. with (diethylamino)sulfur trifluoride. The reaction mixture is refluxed overnight and then quenched with saturated solution of NaHCO₃. The aqueous phase is extracted with ethylacetate. The combined organic layers are washed with brine, dried over MgSO₄, filtrated and concentrated in vacuo to provide 4-bromo-2-difluoromethyl-1-fluoro-benzene (a compound of formula A-Br).

Following the methods of scheme 3, compounds of formulas V and VI may be obtained.

Compounds of formula V: A compound of formula A-Br, bis(pinacolato)diboron, potassium acetate and bis(triphenylphosphine)palladium dichloride are suspensed in dioxane. The suspension is flushed with argon for 30 minutes and refluxed for about 12 hours. The reaction mixture is cooled to room temperature, diluted with ethyl acetate, washed with brine, dried over Na₂SO₄ and concentrated in vacuo to provide a corresponding compound of formula V.

Compounds of formula VI: A compound of formula A-Br, for example a solution of 3-bromo-1,2-dihydro-naphthalene (Adamczyk, M.; Watt, D. S.; Netzel, D. A. *J. Org. Chem.* 1984, 49, 4226–4237) in diethylether is cooled in a dry ice bath and tert.-butyllithium solution is added maintaining T<−65° C. At this temperature stirring is continued for 30 min, then triisopropylborate is added. The reaction mixture is brought to rt and treated with HCl. After 15 min the organic phase is dried (Na₂SO₄), evaporated and precipitated with pentane to provide a corresponding compound of formula VI.

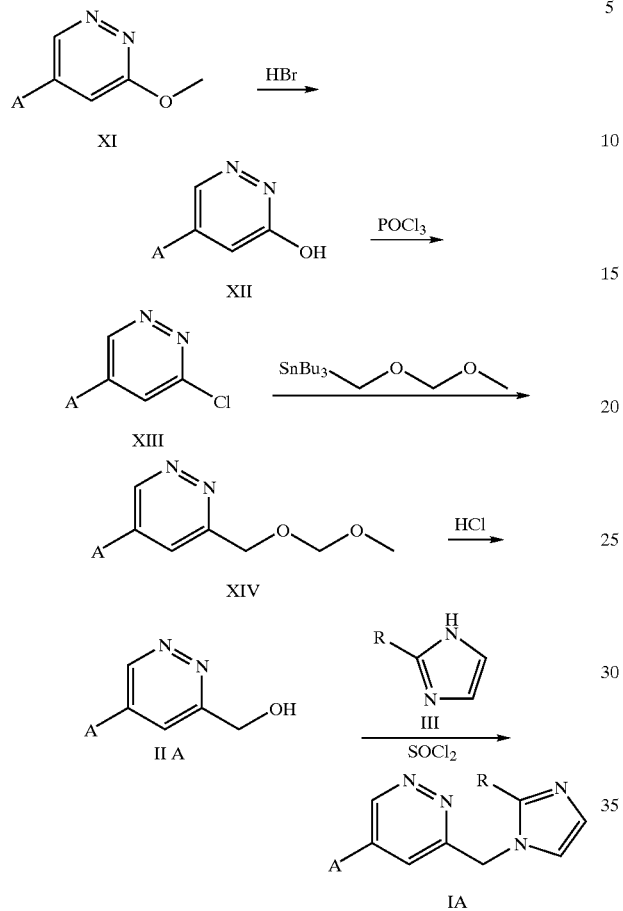

wherein A is the group a), b), c), d), e), f), g), h), i), j) or k) as described above and R is hydrogen or lower alkyl.

In accordance with scheme 4, a compound of formula XI may be obtained in analogy to the following method:

3-Chloro-5-methoxy-pyridazine (Bryant, R. D.; Kunng, F.-A.; South, M. S. *J. Heterocycl. Chem.* (1995), 32(5), 1473–6.), 3-chloro-4-fluorophenylboronic acid, $Cs_2CO_3$ and tris(dibenzylideneacetone)dipalladium chloroform complex are mixed and a solution of tri-tert-butylphosphine in degassed dioxane is added. The mixture is heated at about 90° C. for 22 hours then cooled to room temperature, ethylacetate is added, the solid is filtered and the filtrate is concentrated in vacuo to provide 3-(3-chloro-4-fluoro-phenyl)-5-methoxy-pyridazine (a compound of formula XI).

The compound of formula XI, for example 3-(3-chloro-4-fluoro-phenyl)-5-methoxy-pyridazine in HBr is heated at about 100° C. for 19 hours under argon. The solvent is removed in vacuo and the resulting solid is dissolved in MeOH. The turbid solution is filtered though decalite and the filtrate is concentrated to provide, for example, 6-(3-chloro-4-fluoro-phenyl)-pyridazin-4-ol hydrobromide (XII).

The compound of formula XIII is prepared from a compound of formula XII in phosphorus oxychloride under argon. The mixture was stirred in a 60° C. oilbath for 1.5 hours. The solvent was removed in vacuo and the residue is dissolved in water under icebath cooling. The solution is neutralized with $NaHCO_3$ and the aqueous layer is extracted with $MeCl_2$. The combined extracts are dried over $Na_2SO_4$, filtered and the solvent is removed in vacuo to provide a compound of formula XIII.

This compound of formula XIII and bis-(triphenylphosphine)-palladium(II)-dichloride are treated with a solution of tributyl-methoxymethoxymethyl-stannane (Sawyer J. S.; Kucerovy A.; Macdonald T. L.; McGarvey G. J. *J. Am. Chem. Soc.* (1988), 110, 842–853) in DMF. The mixture is heated at about 100° C. for 4 hours then cooled to room temperature and a saturated KF solution is added. The mixture is stirred for 30 minutes at room temperature and ethyl acetate and water are added. The mixture is filtered and extracted. The combined extracts are dried over $Na_2SO_4$, filtered and the solvent is removed in vacuo to provide a compound of formula XIV.

The obtained compound is dissolved in dioxane and treated with HCl. The reaction mixture is refluxed for 1.5 hours and then cooled to room temperature. Water and ethyl acetate are added. The aqueous layer is extracted with ethyl acetate. The combined organic layers are dried over $Na_2SO_4$, filtered and concentrated in vacuo to provide a compound of formula IIA, which is then treated with a compound of formula III in thionylchloride to a corresponding compound of formula IA.

In accordance with scheme 4, a compound of formula IB may be prepared starting from the compound of formula

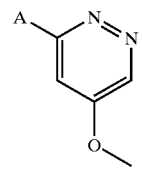

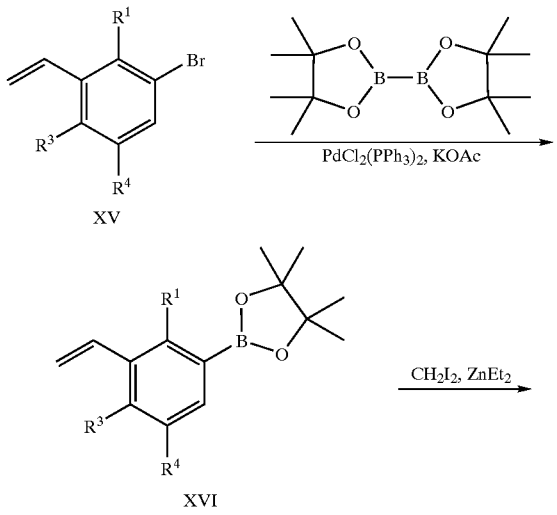

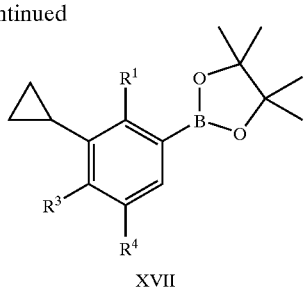

XVII wherein $R^1$, $R^3$ and $R^4$ are described above.

A compound of formula XV may be obtained as follows:

To a suspension of (methyl)triphenyl-phosphonium bromide in THF are added at −78° C. BuLi and a corresponding bromo-benzaldehyde. The reaction mixture is stirred about 18 hours at r.t. After work-up and purification by chromatography a compound of formula XV is obtained.

The compound of formula XV, bis(pinacolato)diboron, potassium acetate and bis(triphenylphosphine)palladium dichloride are suspensed in dioxane. The suspension is flushed with argon for 30 minutes and refluxed for 12 hours. The reaction mixture is cooled to room temperature, diluted with ethyl acetate, washed with brine, dried over $Na_2SO_4$ and concentrated in vacuo to provide a compound of formula XVI.

To a corresponding solution of 4,4,5,5-tetramethyl-2-(3-vinyl-phenyl)-[1,3,2]dioxaborolane (XVI) in toluene are added a diethylzink solution and diiodomethane. The reaction mixture is stirred for 1 hour at room temperature and then refluxed for 3 hours. The reaction mixture is poured on sat. $NH_4Cl$ solution and is extracted with ethylacetate. The combined organic layers are washed with brine, dried over $MgSO_4$, filtrated and concentrated to provide a corresponding cyclopropyl-substituted compound of formula XVII.

Pharmaceutically acceptable salts can be manufactured according to methods which are known per se and familiar to any person skilled in the art. The acid addition salts of compounds of formulas IA or IB are especially well suited for pharmaceutical use.

As mentioned earlier, the compounds of formula IA and IB and their pharmaceutically acceptable acid addition salts possess valuable pharmacodynamic properties. They are NMDA-receptor subtype 2B selective blockers, which have a key function in modulating neuronal activity and plasticity which makes them key players in mediating processes underlying development of CNS as well as learning and memory formation.

The compounds were investigated in accordance with the test given hereinafter.

Test Method $^3$H-Ro 25-6981 binding (Ro 25-6981 is [R-(R*,S*)]-α-(4-hydroxy-phenyl)-β-methyl-4-(phenyl-methyl)-1-piperidine propanol)

Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, EDTA 10 mM, pH 7.1 buffer. The homogenate was centrifuged at 48,000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

$^3$H-Ro 25-6981 binding experiments were performed using a Tris-HCl 50 mM, pH 7.4 buffer. For displacement experiments 5 nM of $^3$H-Ro 25-6981 were used and non specific binding was measured using 10 mM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zürich, Switzerland). The filters were washed 5 times with cold buffer. The radioactivity on the filter was counted on a Packard Top-coullt microplate scintillation counter after addition of 40 mL of microscint 40 (Canberra Packard S.A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits.

The $IC_{50}$ (µM) of preferred compounds of formula I, tested in accordance with the above mentioned method, is <0.1 µM.

Examples of such compounds are:

| Example-No. | $IC_{50}$ (µM) | Example-No. | $IC_{50}$ (µM) |
|---|---|---|---|
| 1 | 0.021 | 31 | 0.031 |
| 3 | 0.038 | 34 | 0.068 |
| 4 | 0.027 | 35 | 0.025 |
| 6 | 0.017 | 36 | 0.077 |
| 9 | 0.034 | 38 | 0.054 |
| 11 | 0.029 | 39 | 0.024 |
| 12 | 0.022 | 41 | 0.041 |
| 13 | 0.011 | 42 | 0.048 |
| 14 | 0.02 | 45 | 0.057 |
| 15 | 0.016 | 48 | 0.035 |
| 16 | 0.01 | 49 | 0.034 |
| 24 | 0.047 | 50 | 0.029 |
| 25 | 0.058 | 52 | 0.026 |
| 26 | 0.012 | 58 | 0.037 |
| 27 | 0.044 | 68 | 0.027 |
| 30 | 0.007 | | |

The compounds of the invention, including compounds of formula IA and IB, and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvants (or "excepients") can be added and include preservatives stabilizers, wetting or emulsifying agents, salts to change the osmotic pressure or to act as buffers. The pharmaceutical preparations can also contain other therapeutically active substances.

Thus, one embodiment of the invention relates to pharmaceutical compositions comprising at least one compound of the invention and a pharmaceutically acceptable carrier or excipient. In another embodiment, the invention relates to a method of treating or alleviating neurodegeneration, depression or pain comprising administering to a patient in need of such therapy a therapeutically effective amount of at least one compound according to the invention.

The dosage can vary within wide limits and will, of course, be fitted to the individual requirements in each particular case. In the case of oral administration the dosage lies in the range of about 0.1 mg per dosage to about 1000 mg per day of a compound of formula I although the upper limit can also be exceeded when this is shown to be indicated.

The following examples illustrate the present invention in more detail. However, they are not intended to limit its scope in any manner. All temperatures are given in degree Celsius.

EXAMPLE 1

5-(3-Chloro-4-fluoro-phenyl)-3-(2-methyl-imidazol-1-yl-methyl)-pyridazine Hydrochloride 5-Chloro-3-(2-methyl-imidazol-1-yl-methyl)-pyridazine (0.07 g, 0.34 mmol), 3-chloro-4-fluorophenylboronic acid (0.076 g, 0.44 mmol), $K_2CO_3$ (0.09 g, 0.67 mmol) and tetrakis(triphenylphosphine)palladium (0.04 g, 0.034 mmol) were mixed and degassed dioxane (1.4 ml) was added. The mixture was refluxed for 44 hours and the solvent was removed in vacuo. The residue was taken in $MeCl_2$, filtrated and the filtrate was concentrated in vacuo. The residue was chromatographed over silica gel ($CH_2Cl_2$—MeOH 98:02) to provide a white foam which was dissolved in MeOH (2 ml). HCl-$Et_2O$ was added to provide 5-(3-chloro-4-fluoro-phenyl)-3-(2-methyl-imidazol-1-yl-methyl)-pyridazine hydrochloride (0.1 g, 77%) as an offwhite solid, MS: m/e=302.7 ($M^+$).

Following the general method of Example 1, the compounds of Examples 2 to Example 67 were prepared.

EXAMPLE 2

3-(2-Methyl-imidazol-1-yl-methyl)-5-(3-trifluoromethyl-phenyl)-pyridazine Hydrochloride The title compound, MS: m/e=319.4 ($M+H^+$), was prepared from 3-trifluoromethylbenzeneboronic acid (commercially available) and 5-chloro-3-(2-methyl-imidazol-1-yl-methyl)-pyridazine.

EXAMPLE 3

5-(4-Fluoro-3-trifluoromethyl-phenyl)-3-(2-methyl-imidazol-1-yl-methyl)-pyridazine hydrochloride The title compound, MS: m/e=337.2 ($M+H^+$), was prepared from 2-(4-fluoro-3-trifluoromethyl-phenyl)-4,4,5,5-tetramethyl-[1,3,2]dioxaborolane and 5-chloro-3-(2-methyl-imidazol-1-ylmethyl)-pyridazine.

EXAMPLE 4

5-(4-Chloro-3-trifluoromethyl-phenyl)-3-(2-methyl-imidazol-1-yl-methyl)-pyridazine hydrochloride The title compound, MS: m/e=353.3 ($M+H^+$), was prepared from 2-(4-chloro-3-trifluoromethyl-phenyl)-4,4,5,5-tetramethyl-[,3,2]dioxaborolane and 5-chloro-3-(2-methyl-imidazol-1-ylmethyl)-pyridazine.

EXAMPLE 5

5-(4-Chloro-3-fluoro-phenyl)-3-(2-methyl-imidazol-1-yl-methyl)-pyridazine hydrochloride The title compound, MS: m/e=303.3 ($M+H^+$), was prepared from 2-(4-chloro-3-fluoro-phenyl)-4,4,5,5-tetramethyl-[1,3,2]dioxaborolane and 5-chloro-3-(2-methyl-imidazol-1-yl-methyl)-pyridazine.

EXAMPLE 6

5-(3-Difluoromethyl-4-fluoro-phenyl)-3-(2-methyl-imidazol-1-yl-methyl)-pyridazine hydrochloride The title compound, MS: m/e=319.4 ($M+H^+$), was prepared from 2-(3-difluoromethyl-4-fluoro-phenyl)-4,4,5,5-tetramethyl-[1,3,2]dioxaborolane and 5-chloro-3-(2-methyl-imidazol-1-yl-methyl)-pyridazine.

EXAMPLE 7

5-(3-Fluoro-5-trifluoromethyl-phenyl)-3-(2-methyl-imidazol-1-yl-methyl)-pyridazine hydrochloride The title compound, MS: m/e 337.2 ($M+H^+$), was prepared from 2-(3-fluoro-5-trifluoromethyl-phenyl)-4,4,5,5-tetramethyl-[1,3,2]dioxaborolane and 5-chloro-3-(2-methyl-imidazol-1-yl-methyl)-pyridazine.

EXAMPLE 8

3-(2-Methyl-imidazol-1-yl-methyl)-5-phenyl-pyridazine hydrochloride

The title compound, MS: m/e=251.2 ($M+H^+$), was prepared from phenylboronic acid and 5-chloro-3-(2-methyl-imidazol-1-ylmethyl)-pyridazine.

EXAMPLE 9

5-[3-(1,1-Difluoro-ethyl)-phenyl]-3-(2-methyl-imidazol-1-yl-methyl)-pyridazine hydrochloride The title compound, MS: m/e=315.4 ($M+H^+$), was prepared from 2-[3-(1,1-difluoro-ethyl)-phenyl]-4,4,5,5-tetramethyl-[1,3,2]dioxaborolane and 5-chloro-3-(2-methyl-imidazol-1-ylmethyl)-pyridazine.

EXAMPLE 10

5-(4-Chloro-phenyl)-3-(2-methyl-imidazol-1-yl-methyl)-pyridazine hydrochloride

The title compound, MS: m/e=285.2 ($M+H^+$), was prepared from 4-chlorophenylboronic (commercial available) and 5-chloro-3-(2-methyl-imidazol-1-yl-methyl)-pyridazine.

EXAMPLE 11

5-[3-(1,1-Difluoro-ethyl)-4-fluoro-phenyl]-3-(2-methyl-imidazol-1-yl-methyl)-pyridazine hydrochloride The title compound, MS: m/e=333.3 ($M+H^+$), was prepared from 2-[3-(1,1-difluoro-ethyl)-4-fluoro-phenyl]-4,4,5,5-tetramethyl-[1,3,2]dioxaborolane and 5-chloro-3-(2-methyl-imidazol-1-yl-methyl)-pyridazine.

EXAMPLE 12

3-(2-Methyl-imidazol-1-ylmethyl)-5-naphthalen-2-yl-pyridazine-hydrochloride

The title compound, MS: m/e=301.3 ($M+H^+$), was prepared from naphtylboronic acid and 5-chloro-3-(2-methyl-imidazol-1-yl-methyl)-pyridazine.

EXAMPLE 13

5-(3,4-Dichloro-phenyl)-3-(2-methyl-imidazol-1-yl-methyl)-pyridazine hydrochloride The title compound, MS: m/e=319.2 ($M^+$), was prepared from 3,4-dichlorophenylboronic acid and 5-chloro-3-(2-methyl-imidazol-1-yl-methyl)-pyridazine.

EXAMPLE 14

5-(3-Cyclopropyl-phenyl)-3-(2-methyl-imidazol-1-yl-methyl)-pyridazine hydrochloride The title compound, MS: m/e=291.3 ($M+H^+$), was prepared from 2-(3-cyclopropyl-phenyl)-4,4,5,5-tetramethyl-[1,3,2]dioxaborolane and 5-chloro-3-(2-methyl-imidazol-1-yl-methyl)-pyridazine.

EXAMPLE 15

5-Benzo[b]thiophen-5-yl-3-(2-methyl-imidazol-1-yl-methyl)-pyridazine hydrochloride The title compound, MS: m/e=307.3 ($M+H^+$), was prepared from 2-benzo[b]thiophen-5-yl-4,4,5,5-tetramethyl-[1,

EXAMPLE 16
5-(4-Fluoro-3-methyl-phenyl)-3-(2-methyl-imidazol-1-yl-methyl)-pyridazine hydrochloride The title compound, MS: m/e=283.1 (M+H$^+$), was prepared from 4-fluoro-3-methylphenylboronic acid (commercially available) and 5-chloro-3-(2-methyl-imidazol-1-yl-methyl)-pyridazine.

EXAMPLE 17
5-(4-Methoxy-phenyl)-3-(2-methyl-imidazol-1-yl-methyl)-pyridazine hydrochloride The title compound, MS: m/e=281.2 (M+H$^+$), was prepared from 4-methoxybenzeneboronic acid and 5-chloro-3-(2-methyl-imidazol-1-yl-methyl)-pyridazine.

EXAMPLE 18
3-(2-Methyl-imidazol-1-yl-methyl)-5-p-tolyl-pyridazine hydrochloride The title compound, MS: m/e=265.3 (M+H$^+$), was prepared from p-tolylboronic acid and 5-chloro-3-(2-methyl-imidazol-1-yl-methyl)-pyridazine.

EXAMPLE 19
5-(2-Chloro-phenyl)-3-(2-methyl-imidazol-1-yl-methyl)-pyridazine hydrochloride The title compound, MS: m/e=285.2 (M+H$^+$), was prepared from 2-chlorophenylboronic acid and 5-chloro-3-(2-methyl-imidazol-1-yl-methyl)-pyridazine.

EXAMPLE 20
5-(3-Chloro-phenyl)-3-(2-methyl-imidazol-1-yl-methyl)-pyridazine hydrochloride The title compound, MS: m/e=285.2 (M+H$^+$), was prepared from 3-chlorophenylboronic acid and 5-chloro-3-(2-methyl-imidazol-1-yl-methyl)-pyridazine.

EXAMPLE 21
5-(3,4-Difluoro-phenyl)-3-(2-methyl-imidazol-1-yl-methyl)-pyridazine hydrochloride The title compound, MS: m/e=287.2 (M+H$^+$), was prepared from 3,4-difluorobenzeneboronic acid and 5-chloro-3-(2-methyl-imidazol-1-yl-methyl)-pyridazine.

EXAMPLE 22
5-(3,5-Dichloro-phenyl)-3-(2-methyl-imidazol-1-yl-methyl)-pyridazine hydrochloride The title compound, MS: m/e=319.3 (M+H$^+$), was prepared from 3,5-dichlorobenzeneboronic acid and 5-chloro-3-(2-methyl-imidazol-1-ylmethyl)-pyridazine.

EXAMPLE 23
5-Benzo[b]thiophen-2-yl-3-(2-methyl-imidazol-1-yl-methyl)-pyridazine hydrochloride The title compound, MS: m/e=307.3 (M+H$^+$), was prepared from benzo[B]thiophene-2-boronic acid and 5-chloro-3-(2-methyl-imidazol-1-yl-methyl)-pyridazine.

EXAMPLE 24
5-(3-Difluoromethyl-5-fluoro-phenyl)-3-(2-methyl-imidazol-1-yl-methyl)-pyridazine hydrochloride The title compound, MS: m/e=319.3 (M+H$^+$), was prepared from 2-(3-difluoromethyl-5-fluoro-phenyl)-4,4,5,5-tetramethyl-[1,3,2]dioxaborolane and 5-chloro-3-(2-methyl-imidazol-1-yl-methyl)-pyridazine.

EXAMPLE 25
5-(3-Difluoromethyl-phenyl)-3-(2-methyl-imidazol-1-yl-methyl)-pyridazine hydrochloride The title compound, MS: m/e=301.3 (M+H$^+$), was prepared from 2-(3-difluoromethyl-phenyl)-4,4,5,5-tetramethyl-[1,3,2]dioxaborolane and 5-chloro-3-(2-methyl-imidazol-1-yl-methyl)-pyridazine.

EXAMPLE 26
5-(4-Chloro-3-difluoromethyl-phenyl)-3-(2-methyl-imidazol-1-yl-methyl)-pyridazine hydrochloride The title compound, MS: m/e=335.3 (M+H$^+$), was prepared from 2-(4-chloro-3-difluoromethyl-phenyl)-4,4,5,5-tetramethyl-[1,3,2]dioxaborolane and 5-chloro-3-(2-methyl-imidazol-1-yl-methyl)-pyridazine.

EXAMPLE 27
5-(6-Methoxy-naphthalen-2-yl)-3-(2-methyl-imidazol-1-yl-methyl)-pyridazine hydrochloride The title compound, MS: m/e 331.4 (M+H$^+$), was prepared from 2-(6-methoxy-naphthalen-2-yl)-4,4,5,5-tetramethyl-[1,3,2]dioxaborolane and 5-chloro-3-(2-methyl-imidazol-1-yl-methyl)-pyridazine.

EXAMPLE 28
5-(6-Difluoromethyl-naphthalen-2-yl)-3-(2-methyl-imidazol-1-yl-methyl)-pyridazine hydrochloride The title compound, MS: m/e 351.4 (M+H$^+$), was prepared from 2-(6-difluoromethyl-naphthalen-2-yl)-4,4,5,5-tetramethyl-[1,3,2]dioxaborolane and 5-chloro-3-(2-methyl-imidazol-1-yl-methyl)-pyridazine.

EXAMPLE 29
3-(2-Methyl-imidazol-1-yl-methyl)-5-(3-trifluoromethoxy-phenyl)-pyridazine hydrochloride The title compound, MS: m/e=335.3 (M+H$^+$), was prepared from 3-(trifluoromethoxy)phenylboronic acid and 5-chloro-3-(2-methyl-imidazol-1-yl-methyl)-pyridazine.

EXAMPLE 30
5-(4-Chloro-3-methyl-phenyl)-3-(2-methyl-imidazol-1-yl-methyl)-pyridazine hydrochloride The title compound, MS: m/e=299.3 (M+H$^+$), was prepared from 2-(4-chloro-3-methyl-phenyl)-4,4,5,5-tetramethyl-[1,3,2]dioxaborolane and 5-chloro-3-(2-methyl-imidazol-1-yl-methyl)-pyridazine.

EXAMPLE 31
5-[3-(1,1-Difluoro-ethyl)-5-fluoro-phenyl]-3-(2-methyl-imidazol-1-yl-methyl)-pyridazine hydrochloride The title compound, MS: m/e=333.3 (M+H$^+$), was prepared from 2-[3-(1,1-difluoro-ethyl)-5-fluoro-phenyl]-4,4,5,5-tetramethyl-[1,3,2]dioxaborolane and 5-chloro-3-(2-methyl-imidazol-1-yl-methyl)-pyridazine.

EXAMPLE 32
5-(5-Difluoromethyl-thiophen-3-yl)-3-(2-methyl-imidazol-1-yl-methyl)-pyridazine hydrochloride The title compound, MS: m/e=307.2 (M+H$^+$), was prepared from 2-(5-difluoromethyl-thiophen-3-yl)-4,4,5,5-tetramethyl-[1,3,2]dioxaborolane and 5-chloro-3-(2-methyl-imidazol-1-yl-methyl)-pyridazine.

EXAMPLE 33
5-Biphenyl-4-yl-3-(2-methyl-imidazol-1-yl-methyl)-pyridazine hydrochloride The title compound, MS: m/e=327.4 (M+H$^+$), was prepared from 4-biphenylboronic acid and 5-chloro-3-(2-methyl-imidazol-1-yl-methyl)-pyridazine.

EXAMPLE 34
5-(3-tert-Butyl-phenyl)-3-(2-methyl-imidazol-1-yl-methyl)-pyridazine hydrochloride The title compound, MS: m/e=307.3 (M+H$^+$), was prepared from 2-(3-tert-butylphenyl)-4,4,5,5-tetramethyl-[1,3,2]dioxaborolane and 5-chloro-3-(2-methyl-imidazol-1-yl-methyl)-pyridazine.

EXAMPLE 35
3-(2-Methyl-imidazol-1-yl-methyl)-5-naphthalen-1-yl-pyridazine hydrochloride The title compound, MS: m/e=301.3 (M+H$^+$), was prepared from 1-naphtylboronic acid and 5-chloro-3-(2-methyl-imidazol-1-yl-methyl)-pyridazine.

EXAMPLE 36
5-(5-Methoxy-naphthalen-1-yl)-3-(2-methyl-imidazol-1-yl-methyl)-pyridazine hydrochloride The title compound, MS: m/e=331.4 (M+H$^+$), was prepared from 2-(5-methoxy-naphthalen-1-yl)-4,4,5,5-tetramethyl-[1,3,2]dioxaborolane and 5-chloro-3-(2-methyl-imidazol-1-yl-methyl)-pyridazine.

EXAMPLE 37
5-Biphenyl-3-yl-3-(2-methyl-imidazol-1-yl-methyl)-pyridazine hydrochloride The title compound, MS: m/e=327.3 (M+H$^+$), was prepared from 3-biphenylboronic acid and 5-chloro-3-(2-methyl-imidazol-1-ylmethyl)-pyridazine.

EXAMPLE 38
5-(3-Methoxy-5-trifluoromethyl-phenyl)-3-(2-methyl-imidazol-1-yl-methyl)-pyridazine hydrochloride The title compound, MS: m/e=349.4 (M+H$^+$), was prepared from 2-(3-methoxy-5-trifluoromethyl-phenyl)-4,4,5,5-tetramethyl-[1,3,2]dioxaborolane and 5-chloro-3-(2-methyl-imidazol-1-yl-methyl)-pyridazine.

EXAMPLE 39
5-[4-Chloro-3-(1,1-difluoro-ethyl)-phenyl]-3-(2-methyl-imidazol-1-yl-methyl)-pyridazine hydrochloride The title compound, MS: m/e=349.4 (M+H$^+$), was prepared from 2-[4-chloro-3-(1,1-difluoro-ethyl)-phenyl]-4,4,5,5-tetramethyl-[1,3,2]dioxaborolane and 5-chloro-3-(2-methyl-imidazol-1-yl-methyl)-pyridazine.

EXAMPLE 40
5-(7-Difluoromethyl-naphthalen-2-yl)-3-(2-methyl-imidazol-1-yl-methyl)-pyridazine hydrochloride The title compound, MS: m/e=351.3 (M+H$^+$), was prepared from 2-(7-difluoromethyl-naphthalen-2-yl)-4,4,5,5-tetramethyl-[1,3,2]dioxaborolane and 5-chloro-3-(2-methyl-imidazol-1-yl-methyl)-pyridazine.

EXAMPLE 41
5-(4-Chloro-3-methoxy-phenyl)-3-(2-methyl-imidazol-1-yl-methyl)-pyridazine hydrochloride The title compound, MS: m/e=315.3 (M+H$^+$), was prepared from 2-(4-chloro-3-methoxy-phenyl)-4,4,5,5-tetramethyl-[1,3,2]dioxaborolane and 5-chloro-3-(2-methyl-imidazol-1-yl-methyl)-pyridazine.

EXAMPLE 42
5-(3-Isopropyl-phenyl)-3-(2-methyl-imidazol-1-yl-methyl)-pyridazine hydrochloride The title compound, MS: m/e=293.3 (M+H$^+$), was prepared from 2-(3-isopropyl-phenyl)-4,4,5,5-tetramethyl-[1,3,2]dioxaborolane and 5-chloro-3-(2-methyl-imidazol-1-yl-methyl)-pyridazine.

EXAMPLE 43
5-(7-Ethoxy-naphthalen-2-yl)-3-(2-methyl-imidazol-1-yl-methyl)-pyridazine hydrochloride The title compound, MS: m/e=345.4 (M+H$^+$), was prepared from 2-(7-ethoxy-naphthalen-2-yl)-4,4,5,5-tetramethyl-[1,3,2]dioxaborolane and 5-chloro-3-(2-methyl-imidazol-1-ylmethyl)-pyridazine.

EXAMPLE 44
5-(4-Methoxy-naphthalen-1-yl)-3-(2-methyl-imidazol-1-yl-methyl)-pyridazine hydrochloride The title compound, MS: m/e=331.3 (M+H$^+$), was prepared from 2-(4-methoxy-naphthalen-1-yl)-4,4,5,5-tetramethyl-[1,3,2]dioxaborolane and 5-chloro-3-(2-methyl-imidazol-1-yl-methyl)-pyridazine.

EXAMPLE 45
5-Acenaphthen-5-yl-3-(2-methyl-imidazol-1-yl-methyl)-pyridazine hydrochloride The title compound, MS: m/e=327.3 (M+H$^+$), was prepared from 2-acenaphthen-5-yl-4,4,5,5-tetramethyl-[1,3,2]dioxaborolane and 5-chloro-3-(2-methyl-imidazol-1-yl-methyl)-pyridaz

EXAMPLE 46
3-(2-Methyl-imidazol-1-yl-methyl)-5-(2-methyl-naphthalen-1-yl)-pyridazine hydrochloride The title compound, MS: m/e=315.3 (M+H$^+$), was prepared from 4,4,5,5-tetramethyl-2-(2-methyl-naphthalen-1-yl)-[1,3,2]dioxaborolane and 5-chloro-3-(2-methyl-imidazol-1-yl-methyl)-pyridazine.

EXAMPLE 47
5-(2-Methoxy-naphthalen-1-yl)-3-(2-methyl-imidazol-1-yl-methyl)-pyridazine hydrochloride The title compound, MS: m/e=331.3 (M+H$^+$), was prepared from 2-(2-methoxy-naphthalen-1-yl)-4,4,5,5-tetramethyl-[1,3,2]dioxaborolane and 5-chloro-3-(2-methyl-imidazol-1-yl-methyl)-pyridazine.

EXAMPLE 48
5-(7-Methoxy-naphthalen-2-yl)-3-(2-methyl-imidazol-1-yl-methyl)-pyridazine hydrochloride The title compound, MS: m/e 331.3 (M+H$^+$), was prepared from 2-(7-methoxy-naphthalen-2-yl)-4,4,5,5-tetramethyl-[1,3,2]dioxaborolane and 5-chloro-3-(2-methyl-imidazol-1-yl-methyl)-pyridazine.

EXAMPLE 49
5-(3-Methoxy-naphthalen-1-yl)-3-(2-methyl-imidazol-1-yl-methyl)-pyridazine hydrochloride The title compound, MS: m/e 331.3 (M+H$^+$), was prepared from 2-(3-methoxy-naphthalen-1-yl)-4,4,5,5-tetramethyl-[1,3,2]dioxaborolane and 5-chloro-3-(2-methyl-imidazol-1-yl-methyl)-pyridazine.

EXAMPLE 50
5-(4-Fluoro-naphthalen-1-yl)-3-(2-methyl-imidazol-1-yl-methyl)-pyridazine hydrochloride The title compound, MS: m/e=319.3 (M+H$^+$), was prepared from 2-(4-fluoro-naphthalen-1-yl)-4,4,5,5-tetramethyl-[1,3,2]dioxaborolane and 5-chloro-3-(2-methyl-imidazol-1-yl-methyl)-pyridazine.

EXAMPLE 51
5-(3-Difluoromethyl-4-fluoro-phenyl)-3-imidazol-1-yl-methyl-pyridazine hydrochloride The title compound, MS: m/e=305.2 (M+H$^+$), was prepared from 2-(3-difluoromethyl-4-fluoro-phenyl)-4,4,5,5- tetramethyl-[1,3,2]dioxaborolane and 5-chloro-3-imidazol-1-yl-methyl-pyridazine.

EXAMPLE 52
5-(3-Difluoromethyl-4-fluoro-phenyl)-3-(2-ethyl-imidazol-1-ylethyl)-pyridazine hydrochloride The title compound, MS: m/e=333.3 (M+H$^+$), was prepared from 2-(3-difluoromethyl-4-fluoro-phenyl)-4,4,5,5-tetramethyl-[1,3,2]dioxaborolane and 5-chloro-3-(2-ethyl-imidazol-1-ylethyl)-pyridazine.

EXAMPLE 53
5-(7-Methoxy-naphthalen-1-yl)-3-(2-methyl-imidazol-1-yl-methyl)-pyridazine The title compound, MS: m/e=331.4 (M+H$^+$), was prepared from 2-(7-methoxy-naphthalen-1-yl)-4,4,5,5-tetramethyl-[1,3,2]dioxaborolane and 5-chloro-3-(2-methyl-imidazol-1-yl-methyl)-pyridazine.

EXAMPLE 54
5-(6-Methoxy-naphthalen-1-yl)-3-(2-methyl-imidazol-1-yl-methyl)-pyridazine The title compound, MS: m/e=331.4 (M+H$^+$), was prepared from 2-(6-methoxy-naphthalen-1-yl)-4,4,5,5-tetramethyl-[1,3,2]dioxaborolane and 5-chloro-3-(2-methyl-imidazol-1-yl-methyl)-pyridazine.

EXAMPLE 55
3-(2-Methyl-imidazol-1-yl-methyl)-5-(4-methyl-naphthalen-2-yl)-pyridazine hydrochloride The title compound, MS: m/e=351.8 (M+H$^+$), was prepared from 4,4,5,5-tetramethyl-2-(4-methyl-naphthalen-2-yl)-[1,3,2]dioxaborolane and 5-chloro-3-(2-methyl-imidazol-1-yl-methyl)-pyridazine.

EXAMPLE 56
5-(5-Methoxy-naphthalen-2-yl)-3-(2-methyl-imidazol-1-yl-methyl)-pyridazine The title compound, MS: m/e 331.4 (M+H$^+$), was prepared from 2-(5-methoxy-naphthalen-2-yl)-4,4,5,5-tetramethyl-[1,3,2]dioxaborolane and 5-chloro-3-(2-methyl-imidazol-1-yl-methyl)-pyridazine.

EXAMPLE 57
5-(1-Methoxy-naphthalen-2-yl)-3-(2-methyl-imidazol-1-yl-methyl)-pyridazine The title compound, MS: m/e=331.4 (M+H$^+$), was prepared from 2-(1-methoxy-naphthalen-2-yl)-4,4,5,5-tetramethyl-[1,3,2]dioxaborolane and 5-chloro-3-(2-methyl-imidazol-1-yl-methyl)-pyridazine.

EXAMPLE 58
5-(2-Fluoro-3-trifluoromethyl-phenyl)-3-(2-methyl-imidazol-1-yl-methyl)-pyridazine hydrochloride The title compound, MS: m/e=337.4 (M+H$^+$), was prepared from 2-(2-fluoro-3-trifluoromethyl-phenyl)-4,4,5,5-tetramethyl-[1,3,2]dioxaborolane and 5-chloro-3-(2-methyl-imidazol-1-yl-methyl)-pyridazine.

EXAMPLE 59
3-(2-Methyl-imidazol-1-yl-methyl)-5-(4-methyl-naphthalen-1-yl)-pyridazine hydrochloride The title compound, MS: m/e=351.9 (M+H$^+$), was prepared from 4,4,5,5-tetramethyl-2-(4-methyl-naphthalen-1-yl)-[1,3,2]dioxaborolane and 5-chloro-3-(2-methyl-imidazol-1-ylmethyl)-pyridazine.

EXAMPLE 60
3-(2-Methyl-imidazol-1-ylmethyl)-5-phenanthren-9-yl-pyridazine

The title compound, MS: m/e=351.4 (M+H$^+$), was prepared from 4,4,5,5-tetramethyl-2-phenanthren-9-yl-[1,3,2]dioxaborolane and 5-chloro-3-(2-methyl-imidazol-1-yl-methyl)-pyridazine.

EXAMPLE 61
5-(3-Cyclopropyl-5-fluoro-phenyl)-3-(2-methyl-imidazol-1-yl-methyl)-pyridazine The title compound was prepared from 2-(3-cyclopropyl-5-fluoro-phenyl)-4,4,5,5-tetramethyl-[1,3,2]dioxaborolane and 5-chloro-3-(2-methyl-imidazol-1-yl-methyl)-pyridazine. (1H-NMR (300 MHz, CDCl$_3$) δ=9.38 (s, 1H), 6.80–7.55 (m, 6H), 5.50 (s, 2H), 2.41 (s, 3H), 1.92–2.02 (m, 1H), 1.02–1.14 (m, 2H), 0.68–0.78 (m, 2H))

EXAMPLE 62
5-(3-Cyclopropyl-4-fluoro-phenyl)-3-(2-methyl-imidazol-1-yl-methyl)-pyridazine The title compound, MS: m/e=309.4 (M+H$^{30}$), was prepared from 2-(3-cyclopropyl-4-fluoro-phenyl)-4,4,5,5-tetramethyl-[1,3,2]dioxaborolane and 5-chloro-3-(2-methyl-imidazol-1-yl-methyl)-pyridazine.

EXAMPLE 63
5-(7-Fluoro-naphthalen-2-yl)-3-(2-methyl-imidazol-1-yl-methyl)-pyridazine The title compound, MS: m/e=319 (M+H$^+$), was prepared from 7-fluoro-naphthalene-2-boronic acid and 5-chloro-3-(2-methyl-imidazol-1-yl-methyl)-pyridazine.

EXAMPLE 64
5-(5-Fluoro-naphthalen-2-yl)-3-(2-methyl-imidazol-1-yl-methyl)-pyridazine The title compound, MS: m/e=319.4 (M+H$^+$), was prepared from 5-fluoro-naphthalene-2-boronic acid and 5-chloro-3-(2-methyl-imidazol-1-yl-methyl)-pyridazine.

EXAMPLE 65
5-(8-Fluoro-naphthalen-2-yl)-3-(2-methyl-imidazol-1-yl-methyl)-pyridazine The title compound, MS: m/e=319 (M+H$^+$), was prepared from 8-fluoro-naphthalene-2-boronic acid and 5-chloro-3-(2-methyl-imidazol-1-yl-methyl)-pyridazine.

EXAMPLE 66
5-Indan-5-yl-3-(2-methyl-imidazol-1-yl-methyl)-pyridazine hydrochloride The title compound, MS: m/e=291.3 (M+H$^+$), was prepared from (2,3-dihydro-1H-inden-5-yl)boronic acid (Dack, K. N.; Whitlock, G. A. PCT Int. Appl. WO 9929667, 1999; Chem Abstr. 1999, 131, 44740) and 5-chloro-3-(2-methyl-imidazol-1-yl-methyl)-pyridazine.

EXAMPLE 67
3-(2-Methyl-imidazol-1-yl-methyl)-5-(5,6,7,8-tetrahydro-naphthalen-2-yl)-pyridazine hydrochloride The title compound, MS: m/e=305.3 (M+H$^+$), was prepared from 4,4,5,5-tetramethyl-2-(5,6,7,8-tetrahydro-naphthalen-2-yl)-[1,3,2]dioxaborolane and 5-chloro-3-(2-methyl-imidazol-1-yl-methyl)-pyridazine.

EXAMPLE 68
5-(3,4-Dihydro-naphthalen-2-yl)-3-(2-methyl-imidazol-1-yl-methyl)-pyridazine hydrochloride Tetrakis(triphenylphosphine)palladium (0.02 g, 0.017 mmol), biphenyl-2-yl-dicyclohexyl-phosphane (0.005 g, 0.014 mmol), K$_3$PO$_4$ (0.21 g, 1 mmol) and 3,4-dihydro-naphthalene-2-boronic acid (0.13 g, 0.7 mmol) were mixed in degassed toluene (2 ml). 5-Chloro-3-(2-methyl-imidazol-1-yl-methyl)-pyridazine (0.1 g, 0.48 mmol) was added and the mixture was refluxed for 24 hours. After further addition of tetrakis(triphenylphosphine)palladium (0.02 g, 0.017 mmol), biphenyl-2-yl-dicyclohexyl-phosphane (0.005 g, 0.014 mmol) and 3,4-dihydro-naphthalene-2-boronic acid (0.13 g, 0.7 mmol) reflux was continued for another 12 hours. After removal of the solvent in vacuo the residue was dissolved in AcOEt, washed with H$_2$O, dried (Na$_2$SO$_4$) and concentrated in vacuo. The residue was chromatographed over silica gel [gradient CH$_2$Cl$_2$ to 40% (CH$_2$Cl$_2$—MeOH—NH$_4$OH 90:10:1)] to provide a white foam which was dissolved in MeOH (2 ml). HCl-Et$_2$O was added to provide the title compound (0.098 g, 40%) as a light yellow solid, MS: m/e=303.3 (M$^+$).

Following the general method of Example 68, the compounds of Example 69 to Example 72 were prepared.

EXAMPLE 69

5-(7-Methoxy-3,4-dihydro-naphthalen-2-yl)-3-(2-methyl-imidazol-1-yl-methyl)-pyridazine hydrochloride The title compound, MS: m/e=333.3 (M+H$^+$), was prepared from 7-methoxy-3,4-dihydro-naphthalene-2-boronic acid and 5-chloro-3-(2-methyl-imidazol-1-yl-methyl)-pyridazine.

EXAMPLE 70

5-(5,7-Dimethyl-3,4-dihydro-naphthalen-2-yl)-3-(2-methyl-imidazol-1-yl-methyl)-pyridazine hydrochloride The title compound, MS: m/e=331.3 (M+H$^+$), was prepared from 5,7-dimethyl-3,4-dihydro-naphthalene-2-boronic acid and 5-chloro-3-(2-methyl-imidazol-1-yl-methyl)-pyridazine.

EXAMPLE 71

5-(5,8-Dimethyl-3,4-dihydro-naphthalen-2-yl)-3-(2-methyl-imidazol-1-yl-methyl)-pyridazine hydrochloride The title compound, MS: m/e=331.3 (M+H$^+$), was prepared from 5,8-dimethyl-3,4-dihydro-naphthalene-2-boronic acid and 5-chloro-3-(2-methyl-imidazol-1-yl-methyl)-pyridazine.

EXAMPLE 72

5-(5-Methoxy-3,4-dihydro-naphthalen-2-yl)-3-(2-methyl-imidazol-1-yl-methyl)-pyridazine hydrochloride The title compound, MS: m/e=333.3 (M+H$^+$), was prepared from 5-methoxy-3,4-dihydro-naphthalene-2-boronic acid and 5-chloro-3-(2-methyl-imidazol-1-yl-methyl)-pyridazine.

EXAMPLE 73

3-(3-Chloro-4-fluoro-phenyl)-5-(2-methyl-imidazol-1-yl-methyl)-pyridazine

[6-(3-Chloro-4-fluoro-phenyl)-pyridazin-4-yl]-methanol (13 mg, 0.054 mmol) was dissolved in MeCl$_2$ (1 ml) under argon and a drop of DMF was added. The mixture was cooled with an icebath, thionylchloride (0.02 ml, 0.27 mmol) was added dropwise and the reaction mixture was allowed to warm to room temperature. After 30 minutes the reaction mixture was concentrated in vacuo. The residue was dissolved in ethanol and treated with 2-methyl-imidazole (22.3 mg, 0.27 mmol). The reaction mixture was refluxed for 12 hours then cooled to room temperature and concentrated. Ethyl acetate and a saturated NaHCO$_3$ solution were added. The aqueous layer was extracted twice with ethyl acetate. The combined organic layers were dried over Na$_2$SO$_4$, filtered and concentrated in vacuo. The residue was chromatographed over silica gel (CH$_2$Cl$_2$—MeOH 19:1) to provide 3-(3-chloro-4-fluoro-phenyl)-5-(2-methyl-imidazol-1-yl-methyl)-pyridazine (4 mg, 24%) as a light brown oil, MS: m/e=303.2 (M+H$^+$).

Preparation of Intermediates

EXAMPLE 74

5-Chloro-3-(2-methyl-imidazol-1-yl-methyl)-pyridazine 6-(2-Methyl-imidazol-1-ylmethyl)-1H-pyridazin-4-one (3.9 g, 20.5 mmol)) was treated with phosphorus oxychloride (18 ml, 205 mmol) under argon. The mixture was stirred in a 60° C. oilbath for 1.5 hours. The solvent was removed in vacuo and the residue was dissolved in water (100 ml) under icebath cooling. The brown solution was neutralized with solid NaHCO$_3$ and the aqueous layer was extracted with MeCl$_2$ (6×50 ml). The combined extracts were dried over Na$_2$SO$_4$, filtered and the solvent was removed in vacuo to provide 5-chloro-3-(2-methyl-imidazol-1-yl-methyl)-pyridazine (3.1 g, 73%) as a brown solid, MS: m/e=209.3 (M+H$^+$).

Following the general method of example 74, the compounds of examples 75 and 76 were prepared.

EXAMPLE 75

5-Chloro-3-imidazol-1-yl-methyl-pyridazine

The title compound, MS: m/e=195.2 (M+H$^+$), was prepared from 6-imidazol-1-yl-methyl-1H-pyridazin-4-one.

EXAMPLE 76

5-Chloro-3-(2-ethyl-imidazol-1-yl-methyl)-pyridazine

The title compound, MS: m/e 223.2 (M+H$^+$), was prepared from 6-(2-ethyl-imidazol-1-yl-methyl)-1H-pyridazin-4-one.

EXAMPLE 77

6-(2-Methyl-imidazol-1-yl-methyl)-1H-pyridazin-4-one

5-Methoxy-3-(2-methyl-imidazol-1-yl-methyl)-pyridazine (4.25 g, 21 mmol) was dissolved in dioxane (65 ml) and 2N NaOH (42 ml) was added. The mixture was refluxed for 7 hours, cooled to room temperature and quenched with 2N HCl (65 ml). The pH was adjusted to 8 with saturated solution of NaHCO$_3$. The solvent was removed in vacuo and the residue was taken in MeOH (100 ml). After filtration, the solvent was removed in vacuo and diluted with MeOH (50 ml). Silicagel (10 g) was added and the solvent was evaporated. The residue was chromatographed over silica gel (CH$_2$Cl$_2$—MeOH 9:1, 4:1, 2:1) to provide 6-(2-methyl-imidazol-1-yl-methyl)-1H-pyridazin-4-one (4.1 g, 100%) as a pale yellow solid, MS: m/e=191.3 (M+H$^+$).

Following the general method of example 77 the compounds of examples 78 and 79 were prepared.

EXAMPLE 78

6-Imidazol-1-yl-methyl-1H-pyridazin-4-one

The title compound, MS: m/e=177.1 (M+H$^+$), was prepared from 3-imidazol-1-yl-methyl-5-methoxy-pyridazine.

EXAMPLE 79

6-(2-Ethyl-imidazol-1-yl-methyl)-1H-pyridazin-4-one

The title compound, MS: m/e=205.2 (M+H$^+$), was prepared from 3-(2-ethyl-imidazol-1-yl-methyl)-5-methoxy-pyridazine.

EXAMPLE 80

5-Methoxy-3-(2-methyl-imidazol-1-yl-methyl)-pyridazine (5-Methoxy-pyridazin-3-yl)-methanol (5.7 g, 40 mmol) was dissolved in MeCl$_2$ (115 ml) under argon and a drop of DMF was added. The mixture was cooled with an icebath, thionylchloride (3.6 ml, 49 mmol) was added dropwise and the reaction mixture was allowed to warm to room temperature. After 30 minutes the orange solution was cooled to 0° C., and saturated NaHCO$_3$ solution (150 ml) was added dropwise. The aqueous layer was extracted twice with MeCl$_2$. The combined organic layers were dried over Na$_2$SO$_4$, filtered and concentrated in vacuo to provide 5.85 g of a brown oil which was dissolved in dioxane (60 ml) and treated with 2-methyl-imidazole (6.1 g, 74 mmol). The reaction mixture was heated at 100° C. for 2 hours then cooled to room temperature. The solvent was evaporated, and the residue was chromatographed over silica gel (CH$_2$Cl$_2$—MeOH 19:1) to provide 5-methoxy-3-(2-methyl-imidazol-1-ylmethyl)-pyridazine (4.6 g, 62%) as a light brown solid, MS: m/e=205.3 (M+H$^+$).

Following the general method of example 80 the compounds of examples 81 and 82 were prepared.

EXAMPLE 81

3-Imidazol-1-yl-methyl-5-methoxy-pyridazine

The title compound, MS: m/e=191.2 (M+H$^+$), was prepared from (5-methoxy-pyridazin-3-yl)-methanol and imidazole.

EXAMPLE 82

3-(2-Ethyl-imidazol-1-yl-methyl)-5-methoxy-pyridazine

The title compound, MS: m/e=219.3 (M+H$^+$), was prepared from (5-methoxy-pyridazin-3-yl)-methanol and 2-ethylimidazole.

EXAMPLE 83

(5-Methoxy-pyridazin-3-yl)-methanol

5-Methoxy-pyridazine-3-carboxylic acid ethyl ester (8.1 g, 44.5 mmol) was dissolved in ethanol (105 ml) under argon. The reaction mixture was cooled to 0° C. and treated with NaBH$_4$ (3.5 g, 89 mmol). After 10 minutes, the reaction mixture was warmed to room temperature, stirred for 1 hour and treated successively with 2N HCl and saturated sodium bicarbonate to adjust the pH at 8. The solvent was removed in vacuo and the residue was stirred with MeOH (100 ml). The suspension was filtered and the filtrate was concentrated. The residue was chromatographed over silica gel (CH$_2$Cl$_2$—MeOH 19:1) to provide (5-methoxy-pyridazin-3-yl)-methanol (5.2 g, 83%) as a light brown solid, MS: m/e=140 (M$^+$).

EXAMPLE 84

5-Methoxy-pyridazine-3-carboxylic acid ethyl ester

3-Chloro-5-methoxy-pyridazine (Bryant, R. D.; Kunng, F. -A.; South, M. S. *J. Heterocycl. Chem.* (1995), 32(5), 1473–6.) (21 g, 0.145 mol), bis(triphenylphosphine) palladium dichloride (10.2 g, 14.5 mmol) and triethylamine (30.5 ml, 0.218 mol) in ethanol (420 ml) were heated at 120° C. under a 40 bar pressure of carbon monoxide for 5 hours. The reaction mixture was cooled, filtered and concentrated in vacuo. The residue was taken in CH$_2$Cl$_2$ (200 ml), washed with H$_2$O (twice), dried over Na$_2$SO$_4$ and concentrated in vacuo. The crude solid was stirred in Et$_2$O and filtered to provide 22.1 g of a light brown solid which was chromatographed over silica gel (hexane-ethylacetate 99:1 to 50:50) to provide 5-methoxy-pyridazine-3-carboxylic acid ethyl ester (21.1 g, 80%) as a pale yellow solid, MS: m/e=183.2 (M+H$^+$).

EXAMPLE 85

[6-(3-Chloro-4-fluoro-phenyl)-pyridazin-4-yl]-methanol 3-(3-Chloro-4-fluoro-phenyl)-5-methoxymethoxymethyl-pyridazine (0.06 g, 0.21 mmol) was dissolved in dioxane (2 ml) and treated with 1N HCl (0.2 ml, 0.2 mmol). The reaction mixture was refluxed for 1.5 hours then cooled to room temperature. Water and ethyl acetate were added. The aqueous layer was extracted twice with ethyl acetate. The combined organic layers were dried over Na$_2$SO$_4$, filtered and concentrated in vacuo. The residue was chromatographed over silica gel (hexane-ethylacetate 1:1 then 2:8) to provide [6-(3-chloro-4-fluoro-phenyl)-pyridazin-4-yl]-methanol (13 mg, 26%) as a light yellow solid, MS: m/e=239.2 (M+H$^+$).

EXAMPLE 86

3-(3-Chloro-4-fluoro-phenyl)-5-methoxymethoxymethyl-pyridazine

5-Chloro-3-(3-chloro-4-fluoro-phenyl)-pyridazine (535 mg, 2.2 mmol) and bis-(triphenylphosphine) -palladium(II)-dichloride (145 mg, 0.22 mmol) were treated with a solution of tributyl-methoxymethoxymethyl-stannane (Sawyer J. S.; Kucerovy A.; Macdonald T. L.; McGarvey G. J. *J. Am. Chem. Soc.* (1988), 110, 842–853) (964 mg, 2.64 mmol) in DMF (5.3 ml). The mixture was heated at 100° C. for 4 hours then cooled to room temperature and a saturated KEF solution (5.3 ml) was added. The mixture was stirred for 30 minutes at room temperature and ethyl acetate and water were added. The mixture was filtered and extracted 3 times with ethyl acetate. The combined extracts were dried over Na$_2$SO$_4$, filtered and the solvent was removed in vacuo. The residue was chromatographed over silica gel (hexane-ethylacetate 7:3) to provide 3-(3-chloro-4-fluoro-phenyl)-5-methoxymethoxymethyl-pyridazine (370 mg, 60%) as a pale yellow solid, MS: m/e=283.0 (M+H$^+$).

EXAMPLE 87

5-Chloro-3-(3-chloro-4-fluoro-phenyl)-pyridazine

The title compound, MS: m/e=243.2 (M$^+$), was prepared from 6-(3-chloro-4-fluoro-phenyl)-pyridazin-4-ol hydrobromide following the procedure described in example 74.

EXAMPLE 88

6-(3-Chloro-4-fluoro-phenyl)-pyridazin-4-ol hydrobromide 3-(3-Chloro-4-fluoro-phenyl)-5-methoxy-pyridazine (365 mg, 1.53 mmol) in aqueous HBr (48%, 3.6 ml) was heated at 100° C. for 19 hours under argon. The solvent was removed in vacuo and the resulting solid was dissolved in MeOH. The turbid solution was filtered though decalite and the filtrate was concentrated. The crude solid was stirred in MeCl$_2$, filtered and dried to provide 6-(3-chloro-4-fluoro-phenyl)-pyridazin-4-ol hydrobromide (375 mg, 80%) as a beige solid, MS: m/e=225.1 (M+H$^+$).

EXAMPLE 89

3-(3-Chloro-4-fluoro-phenyl)-5-methoxy-pyridazine

3-Chloro-5-methoxy-pyridazine (Bryant, R. D.; Kunng, F. -A.; South, M. S. *J. Heterocycl. Chem.* (1995), 32(5), 1473–6.) (300 mg, 2.08 mmol), 3-chloro-4-fluorophenylboronic acid (724 mg, 4.15 mmol), Cs$_2$CO$_3$ (2 g, 6.2 mmol) and tris(dibenzylideneacetone)dipalladium chloroform complex (96.7 mg, 0.093 mmol) were mixed and a solution of tri-tert-butylphosphine (45.4 mg, 0.22 mmol) in degassed dioxane (6 ml) was added. The mixture was heated at 90° C. for 22 hours then cooled to room temperature, ethylacetate was added, the solid was filtered and the filtrate was concentrated in vacuo. The residue was chromatographed over silica gel (hexane-ethyl acetate 4:1) to provide 3-(3-chloro-4-fluoro-phenyl)-5-methoxy-pyridazine (330 mg, 67%) as an orange solid, MS: m/e=239.3 (M+H⁺).

EXAMPLE 90
2-(4-Chloro-3-fluoro-phenyl)-4,4,5,5-tetramethyl-[1,3,2]dioxaborolane 1-Bromo-4-chloro-3-fluorobenzene (1 g, 4.8 mmol), bis(pinacolato)diboron (1.33 g, 5.3 mmol), potassium acetate (1.4 g, 14.3 mmol) and bis(triphenylphosphine)palladium dichloride (0.2 g, 0.29 mmol) were suspensed in dioxane (20 ml). The yellow suspension was flushed with argon for 30 minutes and refluxed for 12 hours. The reaction mixture was cooled to room temperature, diluted with ethyl acetate, washed with brine, dried over Na$_2$SO$_4$ and concentrated in vacuo. The residue was chromatographed over silica gel (hexane-ethyl acetate 99:1) to provide 2-(4-chloro-3-fluoro-phenyl)-4,4,5,5-tetramethyl-[1,3,2]dioxaborolane (0.7 g, 59%) as a colorless oil, MS: m/e=256.2 (M⁺).

Following the general method of example 90, the compounds of examples 91 to example 133 were prepared.

EXAMPLE 91
2-(4-Fluoro-3-trifluoromethyl-phenyl)-4,4,5,5-tetramethyl-[1,3,2]dioxaborolane The title compound, MS: m/e=290.1 (M⁺), was prepared from 5-bromo-2-fluorobenzotrifluoride.

EXAMPLE 92
2-(4-Chloro-3-trifluoromethyl-phenyl)-4,4,5,5-tetramethyl-[1,3,2]dioxaborolane The title compound, MS: m/e=306.1 (M⁺), was prepared from 5-bromo-2-chlorobenzotrifluoride.

EXAMPLE 93
2-(3-Difluoromethyl-4-fluoro-phenyl)-4,4,5,5-tetramethyl-[1,3,2]dioxaborolane The title compound, MS: m/e=272.1 (M⁺), was prepared from 4-bromo-2-difluoromethyl-1-fluoro-benzene.

EXAMPLE 94
2-(3-Fluoro-5-trifluoromethyl-phenyl)-4,4,5,5-tetramethyl-[1,3,2]dioxaborolane The title compound, MS: m/e=290.1 (M⁺), was prepared from 3-bromo-5-fluorobenzotrifluoride.

EXAMPLE 95
2-[3-(1,1-Difluoro-ethyl)-phenyl]-4,4,5,5-tetramethyl-[1,3,2]dioxaborolane The title compound, MS: m/e=268.2 (M⁺), was prepared from 1-bromo-3-(1,1-difluoro-ethyl)-benzene.

EXAMPLE 96
2-Benzo[b]thiophen-5-yl-4,4,5,5-tetramethyl-[1,3,2]dioxaborolane

The title compound, MS: m/e=260.1 (M⁺), was prepared from 5-bromo-benzo[b]thiophene (Ple, P. A.; Marnett, L. J. *J. Heterocycl. Chem.* (1988), 25(4), 1271–2).

EXAMPLE 97
2-(3-Difluoromethyl-phenyl)-4,4,5,5-tetramethyl-[1,3,2]dioxaborolane The title compound, MS: m/e=254.2 (M⁺), was prepared from 1-bromo-3-difluoromethyl-benzene.

EXAMPLE 98
2-(4-Chloro-3-methyl-phenyl)-4,4,5,5-tetramethyl-[1,3,2]dioxaborolane The title compound, MS: m/e=252.1 (M⁺), was prepared from 5-bromo-2-chlorotoluene.

EXAMPLE 99
2-(3-Methoxy-5-trifluoromethyl-phenyl)-4,4,5,5-tetramethyl-[1,3,2]dioxaborolane The title compound, MS: m/e=302.1 (M⁺), was prepared from 1-bromo-3-methoxy-5-trifluoromethyl-benzene.

EXAMPLE 100
2-[4-Chloro-3-(1,1-difluoro-ethyl)-phenyl]-4,4,5,5-tetramethyl-[1,3,2]dioxaborolane The title compound, MS: m/e=302.1 (M⁺), was prepared from 4-bromo-1-chloro-2-(1,1-difluoro-ethyl)-benzene.

EXAMPLE 101
2-(4-Chloro-3-methoxy-phenyl)-4,4,5,5-tetramethyl-[1,3,2]dioxaborolane The title compound, MS: m/e=268.1 (M⁺), was prepared from 4-bromo-1-chloro-2-methoxy-benzene.

EXAMPLE 102
2-(3-Isopropyl-phenyl)-4,4,5,5-tetramethyl-[1,3,2]dioxaborolane

The title compound, MS: m/e=246.2 (M⁺), was prepared from 1-bromo-3-isopropylbenzene.

EXAMPLE 103
2-(7-Methoxy-naphthalen-1-yl)-4,4,5,5-tetramethyl-[1,3,2]dioxaborolane The title compound, MS: m/e=284.2 (M⁺), was prepared from 1-bromo-7-methoxy-naphthalene.

EXAMPLE 104
2-[3-(1,1-Difluoro-ethyl)-4-fluoro-phenyl]-4,4,5,5-tetramethyl-[1,3,2]dioxaborolane The title compound, MS: m/e=286.2 (M⁺), was prepared from 4-bromo-2-(1,1-difluoro-ethyl)-1-fluoro-benzene (prepared according to EP Application No. 01101947.8).

EXAMPLE 105
4,4,5,5-Tetramethyl-2-(3-vinyl-phenyl)-[1,3,2]dioxaborolane

The title compound, MS: m/e=230.2 (M⁺), was prepared from 3-bromostryene.

EXAMPLE 106
2-(3-Fluoro-5-vinyl-phenyl)-4,4,5,5-tetramethyl-[1,3,2]dioxaborolane The title compoundwas prepared from 3-bromo-5-fluoro-stryene. 1H-NMR (300 MHz, CDCl$_3$): δ=7.6 (s, 1H), 7.32–7.40 (m, 1H), 7.16–7.26 (m, 1H), 6.70 (dd, 1H), 5.82 (d, 1H), 5.29 (d, 1H), 1.35 (s, 12H).

EXAMPLE 107
2-(4-Fluoro-3-vinyl-phenyl)-4,4,5,5-Tetramethyl-[1,3,2]dioxaborolane The title compound was prepared from 3-bromo-6-fluoro-stryene. 1H-NMR (300 MHz, CDCl$_3$): δ=7.90–7.96 (m, 1H), 7.64–7.70 (m, 1H), 7.03 (dd, 1H), 6.85 (dd, 1H), 5.82 (d, 1H), 5.28 (d, 1H), 1.35 (s, 12H).

EXAMPLE 108
2-(3-Difluoromethyl-5-fluoro-phenyl)-4,4,5,5-tetramethyl-[1,3,2]dioxaborolane The title compound, MS: m/e=272 (M⁺), was prepared from 1-bromo-3-difluoromethyl-5-fluorobenzene.

EXAMPLE 109
2-(4-Chloro-3-difluoromethyl-phenyl)-4,4,5,5-tetramethyl-[1,3,2]dioxaborolane The title compound, MS: m/e=288.1 (M$^+$), was prepared from 4-bromo-1-chloro-2-difluoromethyl-benzene.

EXAMPLE 110
2-(6-Methoxy-naphthalen-2-yl)-4,4,5,5-tetramethyl-[1,3,2]dioxaborolane The title compound, MS: m/e=284.2 (M-F), was prepared from 2-bromo-6-methoxy-naphthalene (commercially available).

EXAMPLE 111
2-(6-Difluoromethyl-naphthalen-2-yl)-4,4,5,5-tetramethyl-[1,3,2]dioxaborolane The title compound, MS: m/e=304.2 (M$^+$), was prepared from 2-bromo-6-difluoromethylnaphthalene.

EXAMPLE 112
2-[3-(1,1-Difluoro-ethyl)-5-fluoro-phenyl]-4,4,5,5-tetramethyl-[1,3,2]dioxaborolane The title compound, MS: m/e=286.2 (M$^+$), was prepared from 1-bromo-3-(1,1-difluoro-ethyl)-5-fluoro-benzene.

EXAMPLE 113
2-(5-Difluoromethyl-thiophen-3-yl)-4,4,5,5-tetramethyl-[1,3,2]dioxaborolane The title compound, MS: m/e=260.3 (M$^+$), was prepared from 4-bromo-2-difluoromethyl-thiophene.

EXAMPLE 114
2-(3-tert-Butyl-phenyl)-4,4,5,5-tetramethyl-[1,3,2]dioxaborolane The title compound, MS: m/e=260 (M$^+$), was prepared from 2-bromo-3-tert-butylbenzene (prepared according to patent EP 627400).

EXAMPLE 115
2-(5-Methoxy-naphthalen-1-yl)-4,4,5,5-tetramethyl-[1,3,2]dioxaborolane The title compound, MS: m/e=284.2 (M$^+$), was prepared from 1-bromo-5-methoxy-naphthalene.

EXAMPLE 116
2-(7-Difluoromethyl-naphthalen-2-yl)-4,4,5,5-tetramethyl-[1,3,2]dioxaborolane The title compound, MS: m/e=304 (M$^+$), was prepared from 2-bromo-7-difluoromethylnaphthalene.

EXAMPLE 117
2-(7-Ethoxy-naphthalen-2-yl)-4,4,5,5-tetramethyl-[1,3,2]dioxaborolane The title compound, MS: m/e=298 (M$^+$), was prepared from 2-bromo-7-ethoxynaphthalene.

EXAMPLE 118
2-(4-Methoxy-naphthalen-1-yl)-4,4,5,5-tetramethyl-[1,3,2]dioxaborolane The title compound, MS: m/e=284 (M$^+$), was prepared from 1-bromo-4-methoxy-naphthalene.

EXAMPLE 119
2-Acenaphthen-5-yl-4,4,5,5-tetramethyl-[1,3,2]dioxaborolane

The title compound, MS: m/e=280 (M$^+$), was prepared from 5-bromoacenaphthalene.

EXAMPLE 120
4,4,5,5-Tetramethyl-2-(2-methyl-naphthalen-1-yl)-[1,3,2]dioxaborolane The title compound, MS: m/e=286 (M$^+$), was prepared from 1-bromo-2-methyl-naphthalene.

EXAMPLE 121
2-(2-Methoxy-naphthalen-1-yl)-4,4,5,5-tetramethyl-[1,3,2]dioxaborolane The title compound, MS: m/e=284 (M$^+$), was prepared from 1-bromo-2-methoxy-naphthalene.

EXAMPLE 122
2-(7-Methoxy-naphthalen-2-yl)-4,4,5,5-tetramethyl-[1,3,2]dioxaborolane The title compound, MS: m/e=284 (M$^+$), was prepared from 2-bromo-7-methoxynaphthalene.

EXAMPLE 123
2-(3-Methoxy-naphthalen-1-yl)-4,4,5,5-tetramethyl-[1,3,2]dioxaborolane The title compound, MS: m/e=284 (M$^+$), was prepared from 1-bromo-3-methoxy-naphthalene.

EXAMPLE 124
2-(4-Fluoro-naphthalen-1-yl)-4,4,5,5-tetramethyl-[1,3,2]dioxaborolane The title compound, MS: m/e=272 (M$^+$), was prepared from 1-bromo-4-fluoronaphalene

EXAMPLE 125
2-(7-Methoxy-naphthalen-1-yl)-4,4,5,5-tetramethyl-[1,3,2]dioxaborolane The title compound was prepared from 1-bromo-7-methoxynaphalene. 1H-NMR (300 MHz, CDCl$_3$): δ=8.22 (s, 1H), 8.02 (d, 1H), 7.84 (d, 1H), 7.72 (d, 1H), 7.33 (t, 1H), 7.16 (s, 1H), 3.94 (s, 3H), 1.42 (s, 12H).

EXAMPLE 126
2-(6-Methoxy-naphthalen-1-yl)-4,4,5,5-tetramethyl-[1,3,2]dioxaborolane The title compound was prepared from 1-bromo-6-methoxynaphalene (prepared according to patent WO 9000164A1). 1H-NMR (300 MHz, CDCl$_3$): δ=8.67 (d, 1H), 7.91 (d, 1H), 7.82 (d, 1H), 7.73 (d, 1H), 7.43 (t, 1H), 7.10–7.22 (m, 1H), 3.92 (s, 3H), 1.42 (s, 12H).

EXAMPLE 127
4,4,5,5-Tetramethyl-2-(4-methyl-naphthalen-2-yl)-[1,3,2]dioxaborolane The title compound, MS: m/e=268 (M$^+$), was prepared from 2-bromo-6-methylnaphalene (prepared according to patent WO 0064891A1).

EXAMPLE 128
2-(5-Methoxy-naphthalen-2-yl)-4,4,5,5-tetramethyl-[1,3,2]dioxaborolane The title compound, MS: m/e=284 (M$^+$), was prepared from 2-bromo-5-methoxynaphalene (prepared according to patent WO 0064891A1).

EXAMPLE 129
2-(1-Methoxy-naphthalen-2-yl)-4,4,5,5-tetramethyl-[1,3,2]dioxaborolane The title compound, MS: m/e=284 (M$^+$), was prepared from 2-bromo-1-methoxynaphthalene.

EXAMPLE 130
2-(2-Fluoro-3-trifluoromethyl-phenyl)-4,4,5,5-tetramethyl-[1,3,2]dioxaborolane The title compound, MS: m/e=290 (M$^+$), was prepared from 3-bromo-2-fluorobenzotrifluoride (commercially available).

EXAMPLE 131
4,4,5,5-Tetramethyl-2-(4-methyl-naphthalen-1-yl)-[1,3,2]dioxaborolane The title compound, MS: m/e=268 (M$^+$), was prepared from 1-bromo-4-methylnaphthalene (commercial available).

EXAMPLE 132
4,4,5,5-Tetramethyl-2-phenanthren-9-yl-[1,3,2]dioxaborolane

The title compound, MS: m/e=304 (M$^+$), was prepared from 9-bromophenanthrene (commercially available).

EXAMPLE 133
4,4,5,5-Tetramethyl-2-(5,6,7,8-tetrahydro-naphthalen-2-yl)-[1,3,2]dioxaborolane The title compound, MS: m/e=258.3 (M$^+$), was prepared from trifluoro-methanesulfonic acid 5,6,7,8-tetrahydro-naphthalen-2-yl ester (Han, X.; Stoltz, B. M.; Corey, E. J. *J. Am. Chem. Soc.* 1999, 121, 7600–7605).

EXAMPLE 134
2-(3-Cyclopropyl-phenyl)-4,4,5,5-tetramethyl-[1,3,2]dioxaborolane To a solution of 4,4,5,5-tetramethyl-2-(3-vinyl-phenyl)-[1,3,2]dioxaborolane (300 mg, 1.3 mmol) in toluene (10 ml) were added diethylzinc solution (1.1 N in toluene, 5.22 ml, 5.74 mmol) and diiodomethane (8.7 ml, 33 mmol). The reaction mixture was stirred for 1 hour at room temperature and then refluxed for 3 hours. The reaction mixture was poured on sat. NH$_4$Cl solution (20 ml) and was extracted with ethyl acetate. The combined organic layers were washed with brine, dried over MgSO$_4$, filtered and concentrated in vacuo to provide 2-(3-cyclopropyl-phenyl)-4,4,5,5-tetramethyl-[1,3,2]dioxaborolane (69% yield), 1H-NMR (300 MHz, CDCl$_3$): δ=7.12–7.82 (m, 4H), 1.35 (s, 12H), 1.28 (t, 1H), 0.90–0.96 (m, 2H), 0.72–0.78 (m, 2H).

Following the general method of example 134 the compounds of examples 135 and 136 were prepared.

EXAMPLE 135
2-(3-Cyclopropyl-4-fluoro-phenyl)-4,4,5,5-tetramethyl-[1,3,2]dioxaborolane The title compound, MS: m/e=262(M$^+$), was prepared from 2-(4-fluoro-3-vinylphenyl)-4,4,5,5-tetramethyl-[1,3,2]dioxaborolane following the procedure described in example 134.

EXAMPLE 136
2-(3-Cyclopropyl-5-fluoro-phenyl)-4,4,5,5-tetramethyl-[1,3,2]dioxaborolane The title compound, MS: m/e=262(M$^+$), was prepared from 2-(5-fluoro-3-vinylphenyl)-4,4,5,5-tetramethyl-[1,3,2]dioxaborolane following the procedure described in example 134.

EXAMPLE 137
3,4-Dihydro-naphthalene-2-boronic acid

A solution of 3-bromo-1,2-dihydro-naphthalene (7.7 g, 37 mmol) (Adamczyk, M.; Watt, D. S.; Netzel, D. A. *J. Org. Chem.* 1984, 49, 4226–4237) in diethylether (370 ml) was cooled in a dry ice bath and tert.-butyllithium solution (50 ml of a 1.5 M solution in pentane) was added maintaining T<–65° C. At this temperature stirring was continued for 30 min, then triisopropylborate (17.3 ml, 75 mmol) was added. The reaction mixture was brought to rt and treated with 3N HCl (100 ml). After 15 min the organic phase was dried (Na$_2$SO$_4$), evaporated and precipitated with pentane to provide the title compound (3.83 g, 60%) as a white solid material. MS: m/e=173 (M–H$^-$).

Following the general method of Example 137 the compounds of Examples 138 to Example 144 were prepared.

EXAMPLE 138
5-Fluoro-naphthalene-2-boronic acid

The title compound was obtained by reaction of 2-bromo-5-fluoro-naphthalene with tert.-butyllithium solution followed by triisopropylborate and HCl. MS: m/e=189(M$^-$).

EXAMPLE 139
8-Fluoro-naphthalene-2-boronic acide

The title compound was obtained by reaction of 2-bromo-8-fluoro-naphthalene with tert.-butyllithium solution followed by triisopropylborate and HCl. MS: m/e=189 (M$^-$).

EXAMPLE 140
7-Fluoro-naphthalene-2-boronic acid

The title compound was obtained by reaction of 2-bromo-7-fluoro-naphthalene with tert.-butyllithium solution followed by triisopropylborate and HCl. 1H-NMR (300 MHz, DMSO): δ=8.35 (s, 1H), 8.22 (br. s, 2H), 7.82–8.04 (m, 3H), 7.69 (d, 1H), 7.44 (t, 1H).

EXAMPLE 141
7-Methoxy-3,4-dihydro-naphthalene-2-boronic acid

The title compound was obtained as a white solid material by reaction of 3-bromo-6-methoxy-1,2-dihydro-naphthalene with tert.-butyllithium solution followed by triisopropylborate and 3N HCl. MS: m/e=263 (M+OAc$^-$).

EXAMPLE 142
5,7-Dimethyl-3,4-dihydro-naphthalene-2-boronic acid

The title compound was obtained as a white solid material by reaction of 3-bromo-6,8-dimethyl-1,2-dihydro-naphthalene with tert.-butyllithium solution followed by triisopropylborate and 3N HCl. MS: m/e=261 (M+OAc$^-$).

EXAMPLE 143
5,8-Dimethyl-3,4-dihydro-naphthalene-2-boronic acid

The title compound was obtained as a white crystalline material by reaction of 3-bromo-5,8-dimethyl-1,2-dihydro-naphthalene with tert.-butyllithium solution followed by triisopropylborate and 3N HCl. MS: m/e=261 (M+OAc$^-$).

EXAMPLE 144
5-Methoxy-3,4-dihydro-naphthalene-2-boronic acid

The title compound was obtained as a white crystalline material by reaction of 3-bromo-8-methoxy-1,2-dihydro-naphthalene with tert.-butyllithium solution followed by triisopropylborate and 3N HCl. MS: m/e=203 (M–H$^-$).

EXAMPLE 145
4-Bromo-2-difluoromethyl-1-fluoro-benzene

5-Bromo-2-fluorobenzaldehyde (2 g, 9.8 mmol) in CH$_2$Cl$_2$ (50 ml) was treated at 0° C. with (diethylamino) sulfur trifluoride (2 ml, 14.8 mmol). The reaction mixture was refluxed overnight and then quenched with saturated solution of NaHCO$_3$. The aqueous phase was extracted with ethyl acetate. The combined organic layers were washed with brine, dried over MgSO$_4$, filtered and concentrated in vacuo. The residue was chromatographed over silica gel (hexane-ethyl acetate 99:01) to provide 4-bromo-2-difluoromethyl-1-fluoro-benzene (1.55 g, 70%) as a colorless oil, MS: m/e=226.0 (M+H$^+$).

Following the general method of Example 145 the compounds of Examples 146 to Example 152, 157 and 159, were prepared.

EXAMPLE 146
1-Bromo-3-(1,1-difluoro-ethyl)-benzene

The title compound, MS: m/e=221.0 (M$^+$), was prepared from 3-bromoacetophenone (commercially available).

EXAMPLE 147
1-Bromo-3-difluoromethyl-benzene

The title compound, MS: m/e=207.0 (M$^+$), was prepared from 3-bromo-benzaldehyde (commercially available).

EXAMPLE 148
4-Bromo-1-chloro-2-(1,1-difluoro-ethyl)-benzene

The title compound, MS: m/e=255.4 (M$^+$), was prepared from 1-(5-bromo-2-chloro-phenyl)-ethanone (prepared according to patent: DD 236726).

EXAMPLE 149
1-Bromo-3-difluoromethyl-5-fluorobenzene

The title compound, MS: m/e=272 (M$^+$), was prepared from 3-bromo-5-fluorobenzaldehyde (prepared according to patent WO 0066556).

EXAMPLE 150
4-Bromo-2-difluoromethyl-thiophene

The title compound, MS: m/e=214.0 (M+H$^+$), was prepared from 4-bromothiophen-2-carbaldehyde (commercially available).

EXAMPLE 151
2-bromo-6-difluoromethylnaphthalene

The title compound, MS: m/e=258 (M+H$^+$), was prepared from 2-bromo-6-carbaldehyde-naphthalene (prepared according to patent WO 9833778).

EXAMPLE 152
1-Bromo-3-(1,1-difluoro-ethyl)-5-fluoro-benzene

The title compound was prepared from 1-(3-bromo-5-fluoro-phenyl)-ethanone. 1H-NMR (300 MHz, CDCl$_3$): δ=7.44 (s, 1H), 7.31 (d, 1H), 7.16 (d, 1H), 1.90 (t, 3H).

EXAMPLE 153
1-(3-Bromo-5-fluoro-phenyl)-ethanone

To a solution of 1-(3-bromo-5-fluoro-phenyl)-ethanol (2.9 g, 13.2 mmol) in methylene chloride (150 ml) was added at room temperature pyridinium dichromate (3.98 g). The reaction mixture was stirred for 4 hours at room temperature and the solvent was removed in the presence of silica gel. The crude product was purified by chromatography over silica gel to provide 1-(3-bromo-5-fluoro-phenyl)-ethanone (1.39 g, 45%) as a light yellow solid, MS: m/e=216.1 (M$^+$).

EXAMPLE 154
1-(3-Bromo-5-fluoro-phenyl)-ethanol

To a solution of 3-bromo-5-fluorobenzaldehyde (6.0 g, 29.6 mmol, prepared according to patent WO 0066556) in THF (100 ml) was added dropwise at 0° C. methylmagnesiumchloride (3N in THF, 12 ml). The reaction mixture was stirred for 3 hours at room temperature and then sat. NH$_4$Cl solution was added. The aqueous phase was extracted twice with ethyl acetate. The combined organic layers were washed with water, dried over MgSO$_4$, filtered and the solvent was removed in vacuo. The crude product was purified by chromatography over silica gel to yield 1-(3-bromo-5-fluoro-phenyl)-ethanol (2.9 g, 45%), 1H-NMR (300 MHz, CDCl$_3$): δ=7.31 (s, 1H), 7.14 (d, 1H), 7.04 (d, 1H), 4.82–4.94 (m, 1H), 1.51 (d, 3H).

EXAMPLE 155
4-Bromo-1-chloro-2-difluoromethyl-benzene

To a solution of NaNO$_2$ 0.59 g, 8.6 mmol) in sulfuric acid (6 ml) and acetic acid (7 ml) was added portionwise under cooling 4-chloro-3-difluoromethyl-phenylamine (1.5 g, 8.4 mmol). This mixture was added dropwise to a vigorously stirred solution of CuBr in HBr at 0° C. The mixture was stirred for 45 min at room temperature and then poured on ice-water. The aqueous phase was extraction with CH$_2$Cl$_2$. The combined organic layers were dried over MgSO$_4$, the solvent was removed under reduced pressure to provide 4-bromo-1-chloro-2-difluoromethyl-benzene (64%), MS: m/e=242.0 (M+1).

EXAMPLE 156
4-Chloro-3-difluoromethyl-phenylamine

To a suspension of iron powder (16 g) in acetic acid (95 ml) was added 1-chloro-2-difluoromethyl-4-nitro-benzene (5.1 g, 15 mmol) and the reaction mixture was heated to 115° C. for 15 minutes. The mixture was filtered and the residue was washed with acetic acide and CH$_2$Cl$_2$. Evaporation of the solvent gave the crude product. It was further purified by chromatography over silica gel to give 4-chloro-3-difluoromethyl-phenylamine (76%), MS: m/e=177.1 (M$^+$).

EXAMPLE 157
1-Chloro-2-difluoromethyl-4-nitro-benzene

The title compound, MS: m/e=207.0 (M$^+$), was prepared from 2-chloro-5-nitrobenzaldehyde following the procedure described in example 145.

EXAMPLE 158
1-Bromo-5-methoxy-naphthalene

A suspension of 1-bromo-5-hydroxy-naphthalene (1.56 g, 7.0 mmol, prepared according to patent WO0146181), K$_2$CO$_3$ (1.45 g, 10.5 mmol), tetrabutylammonium chloride (15 mg, 0.05 mmol) and dimethyl sulfate (1.32 ml, 10.5 mmol) in MeCN was refluxed for 1 hour. After the addition of water, the aqueous phase was extracted three times with CH$_2$Cl$_2$. The combined organic layers were washed with water, dried over MgSO$_4$, filtered and the solvent was removed under reduced to provide 1-bromo-5-methoxy-naphthalene (1.05 g, 64%) as a white solid, MS: m/e=236 (M$^+$).

EXAMPLE 159
2-bromo-7-difluoromethyl-naphthalene

The title compound, MS: m/e=256 (M$^+$), was prepared from 7-bromo-2-naphthalene-carbaldehyde following the procedure described in example 145.

EXAMPLE 160
7-Bromo-2-naphthalene-carbaldehyde

To a solution of 7-bromo-naphthalene-2-yl)methanol (1.37 g, 5.8 mmol) in CH$_2$Cl$_2$ was reacted (according to A. J. Mancuso and D. Swern, Synthesis, 1981, 165) with oxalylchloride (0.55 ml, 6 mmol), DMSO (0.9 ml, 13 mmol) and NEt$_3$ (0.73 ml, 29 mmol) to provide 7-bromo-2-naphthalene-carbaldehyde (quantitative yield), MS: m/e=234 (M$^+$).

EXAMPLE 161
7-Bromo-naphthalene-2-yl-methanol

To a solution of 7-bromo-naphthalene-2-carboxylic acid methyl ester (1.4 g, 5.3 mmol, prepared according to patent EP 483667 A2) in THF (50 ml) was added DIBAL-H (15.8 ml, 1M solution in THF) and the reaction mixture was stirred for 1 hour. After workup, 7-bromo-naphthalene-2-yl-methanol was ontained in quantitative yield, MS: m/e=236 (M$^+$)

EXAMPLE 162
2-Bromo-7-ethoxynaphthalene

To a solution of 7-bromo-naphth-2-ol (1.0 g, 4.5 mmol, prepared according to patent WO 0146187 A1) in acetonitrile (10 ml) was added diethyl sulfate (1.04 g, 6.7 mmol), $K_2CO_3$ (0.92 g) and tetrabutylammonium bromide (10 mg). The reaction mixture was refluxed for 1 hour, poured on water and extracted with $CH_2Cl_2$. The combined organic layers were dried over $MgSO_4$, filtered and the solvent was removed under reduced pressure to provide 2-bromo-7-ethoxynaphthalene (89%), MS: m/e=252 (M$^+$).

EXAMPLE 163
2-Bromo-7-methoxynaphthalene

The title compound, MS: m/e=236(M$^+$), was prepared from 7-bromo-naphth-2-ol and dimethylsulfate following the procedure described in example 162.

EXAMPLE 164
1-Bromo-3-methoxy-5-trifluoromethyl-benzene

The title compound, MS: m/e=254(M$^+$), was prepared from 5-methoxy-3-(trifluoromethyl)-aniline following the procedure described in example 155.

EXAMPLE 165
2-Bromo-8-fluoro-naphthalene

To a solution of $BF_3$-etherate (0.86 ml, 1.25 M in THF, 6.5 mmol) in 12 ml dimethoxyethane was added at −5° C. a solution of 8-amino-2-bromo-naphthalene (1.20 g, 5.4 mmol) in dimethoxyethane (12 ml) over a periode of 35 min. After 1 hour a solution of tert-butylnitrite (0.62 ml, 5.4 mmol) in dimethoxyethane (24 ml) was added and the mixture was stirred for two hours at r.t. and the solvent was removed under reduced pressure. Chlorbenzene (120 ml) was added and the reaction mixture was refluxed for 50 min and the mixture was concentrated. The solid was diluted in methylene chloride and washed with $NaHCO_3$. The organic phase was dried over $MgSO_4$, filtered and reduced to give the crude product. Chromatography on silica gel (hexane) afforded 721 mg (59%) of the product as a brown oil. MS: m/e=242 (M$^+$).

EXAMPLE 166
8-Amino-2-bromo-naphthalene

To a suspension of iron powder (1.66 g) in 25 ml water and 25% HCL (1.7 ml) was added 2-bromo-8-nitro-naphthalene (2.15 g, 8.5 mmol) and the reaction mixture was refluxed for 2 hours. The aqueous phase was extracted with ethyl acetate to give the crude product. Chromatography on silica gel (hexane/ethyl acetate 1/9 to 2/3) afforded 1.17 g (62%) of the product as brown oil. MS: m/e=222.2 (M$^+$).

EXAMPLE 167
2-Bromo-8-nitro-naphthalene

A solution of 2-bromonaphthalene (11.4 g, 55 mmol) in nitric acide (40 ml) and acetic acide (40 ml) was heated to 60° C. for 2 hours and then poured on ice. The mixture was filtered and a yellow solid was obtained. The mixture of mono-nitrated products was separated by chromatography on silica gel (hexane:toluene 95:5) to give 2.15 g (15%) of the title product as yellow solid, MS: m/e=251 (M$^+$).

EXAMPLE 168
2-Bromo-5-fluoro-naphthalene

The title compound, MS: m/e=224 (M$^+$), was prepared from 5-amino-2-bromo-naphthalene following the procedure described in example 165.

EXAMPLE 169
5-Amino-2-bromo-naphthalene

The title compound, MS: m/e=222 (M$^+$), was prepared from 2-bromo-5-nitro-naphthalene following the procedure described in example 166.

EXAMPLE 170
2-Bromo-5-nitro-naphthalene

The title compound, MS: m/e=251 (M$^+$), was prepared from 2-bromo-naphthalene following the procedure described in example 167.

EXAMPLE 171
2-Bromo-7-fluoronaphthalene

The title compound, MS: m/e=224 (M$^+$), was prepared from 7-amino-2-bromo-naphthalene following the procedure described in example 165.

EXAMPLE 172
7-Amino-2-bromo-naphthalene

The title compound was prepared from 2-bromo-7-nitro-naphthalene following the procedure described in example 166. 1H-NMR (300 MHz, CDCl$_3$): δ=7.72 (s, 1H), 7.61 (d, 1H), 7.54 (d, 1H), 7.27 (d, 1H), 6.93 (d, 1H), 6.86 (s, 1H), 3.90 (br. s, 2H).

EXAMPLE 173
2-Bromo-7-nitro-naphthalene

To a solution of $NaNO_2$ (1.1 g, 24 mmol) in sulfuric acid (8.4 ml) was added at 0° C. acetic acid (8.9 ml) and 7-amino-2-nitro-naphthalene (2.1 g, 1mmol). This solution was added to a suspension of CuBr (2.5 g, 39 mmol) in conc. HBr (16 ml) at 0° C. and the mixture was stirred for 1 hour. The mixture was poured on ice and the aqueous phase was extracted with methylene chloride. The crude product was purified by chromatography to give 1.9 g (7.4 mmol, 51%) of the title compound, MS: m/e=251.2 (M$^+$).

EXAMPLE 174
7-Amino-2-nitro-naphthalene

A suspension of 2,7-dinitro-naphthalene in ethylacetate (400 ml) and DMF (4 ml) was hydrogenated over P/C at 50° C. for 2 hours. After work-up and purification by chromatography 2.1 g (11.2 mmol, 24%) of the title compound, MS: m/e=251(M$^+$) was obtained.

EXAMPLE 175
4-Bromo-1-fluoro-2-vinylbenzene

To a suspension of methyl(triphenyl)-phosphonium bromide (15.5 g, 43 mmol) in THF (60 ml) were added at −78° C. BuLi (27 ml, 1.6 M in hexane, 43.2 mmol) and 5-bromo-2-fluoro-benzaldehyde (877 mg, 43 mmol). The reaction mixture was stirred 18 hours at r.t. After work-up and purification by chromatography (hexane/ethyl acetate 9/1 to 4/1) 5.7 g (28.5 mmol, 72%) of the title compound were obtained, 1H-NMR (300 MHz, CDCl$_3$): δ=7.62 (dd, 1H), 7.26–7.36 (m, 1H), 6.93 (t, 1H), 6.79 (dd, 1H), 5.42 (d, 1H).

EXAMPLE 176

5-Bromo-1-fluoro-3-vinylbenzene

The title compound, MS: m/e 200(M$^+$), was prepared from 5-bromo-3-fluorobenzaldehyde following the procedure described in example 175.

EXAMPLE 177

3-Bromo-6-methoxy-1,2-dihydro-naphthalene

Following the Adamczyk-Netzel protocol (Adamczyk, M.; Watt, D. S.; Netzel, D. A. *J. Org. Chem.* 1984, 49, 4226–4237), the title compound was obtained as a colorless oil by reaction of 7-methoxy-1-tetralone first with bromine, then with sodium borohydride and finally with p-toluenesulfonic acid. $^1$H-Nmr (250 MHz, CDCl$_3$): δ=2.76 and 2.86 each: (mc, 2H, C$\underline{H}_2$), 3.76 (s, OC$\underline{H}_3$), 6.54 (d, J=3 Hz, 1H, arom-H), 6.68 (dd, J=8 Hz, J=3 Hz, 1H, arom-$\underline{H}$), 6.75 (s, 1H, C$\underline{H}$=CBr), 7.00 (d, J=8Hz, 1H, arom-$\underline{H}$).

Following the general method of Example 177, the compounds of Examples 178 to 180 were prepared.

EXAMPLE 178

3-Bromo-6,8-dimethyl-1,2-dihydro-naphthalene

The title compound was obtained as a colorless oil by reaction of 5,7-dimethyl-1-tetralone with bromine, sodium borohydride and p-toluenesulfonic acid. MS: m/e=236 (M$^+$).

EXAMPLE 179

3-Bromo-5,8-dimethyl-1,2-dihydro-naphthalene

The title compound was obtained as a colorless oil by reaction of 5,8-dimethyl-1-tetralone with bromine, sodium borohydride and p-toluenesulfonic acid. MS: m/e=236 (M$^+$).

EXAMPLE 180

3-Bromo-8-methoxy-1,2-dihydro-naphthalene

The title compound was obtained as a colorless oil by reaction of 5-methoxy-1-tetralone with bromine, sodium borohydride and p-toluenesulfonic acid. 1H-Nmr (250 MHz, CDCl$_3$): δ=2.74 and 2.94 each: (mc, 2H, C$\underline{H}_2$), 3.82 (s, 3H, OC$\underline{H}_3$), 6.62 (d, J=8 Hz, 1H, arom-$\underline{H}$), 6.75 (s, 1H, C$\underline{H}$=CBr), 6.76 (d, J=8 Hz, 1H, arom-$\underline{H}$), 7.11 (t, J=8 Hz, 1H, arom-$\underline{H}$).

EXAMPLE A

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula 1 | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

EXAMPLE B

Capsule Formulation

| Item | Ingredients | mg/capsule | | | |
|---|---|---|---|---|---|
| | | 5 mg | 25 mg | 100 mg | 500 mg |
| 1. | Compound of formula 1 | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2, and 3 in a suitable mixer for 30 minutes.
2. Add items 4 and 5 and mix for 3 minutes.
3. Fill into a suitable capsule.
4. Add item 5 and mix for three minutes; compress on a suitable press.

What is claimed is:

1. A compound of formula

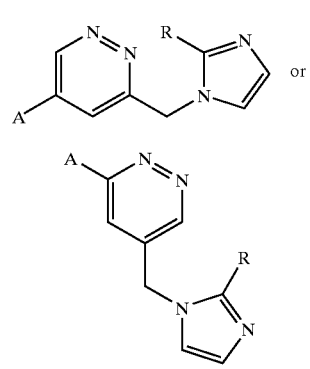

wherein

A is selected from:

a)

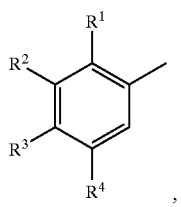

b)

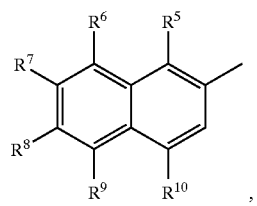

c) 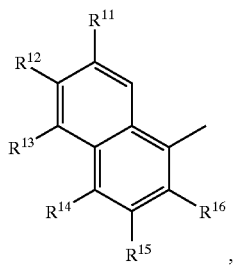

d) 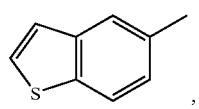

e) 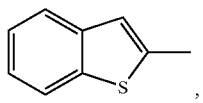

f) 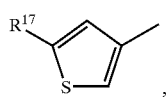

g) 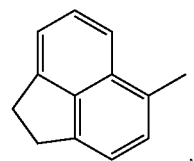

h) 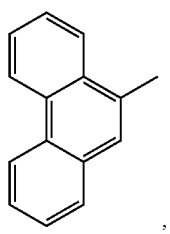

i) 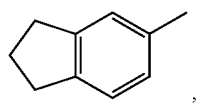

j) 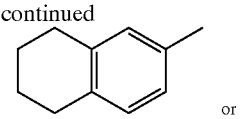

or k) 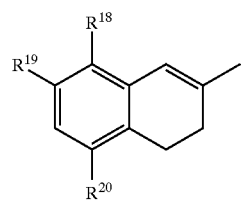

and
R is hydrogen or lower alkyl;
or a pharmaceutically acceptable acid addition salt thereof.

2. The compound of claim 1, wherein A is the group a)

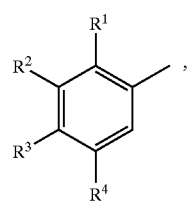

wherein
$R^1$–$R^4$ are each independently selected from hydrogen, halogen, $CF_3$, $CHF_2$, $C(CH_3)F_2$, $C_3$–$C_6$-cycloalkyl, lower alkoxy, lower alkyl, $OCF_3$ and phenyl.

3. The compound of claim 1, wherein A is the group b)

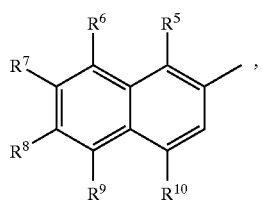

wherein
$R^5$–$R^{10}$ are each independently selected from hydrogen, halogen, lower alkyl, lower alkoxy and $CHF_2$.

4. The compound of claim 1, wherein A is the group c)

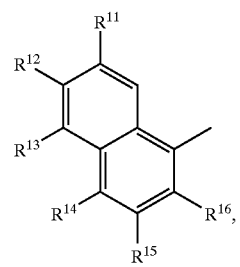

wherein
$R^{11}$–$R^{16}$ are each independently selected from hydrogen, halogen, lower alkoxy and lower alkyl.

5. The compound of claim 1, wherein A is the group

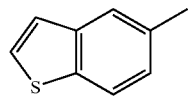 d)

6. The compound of claim 1, wherein A is the group

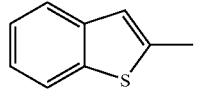 e)

7. The compound of claim 1, wherein A is the group

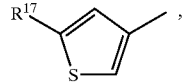 f)

wherein $R^{17}$ is hydrogen or $CHF_2$.

8. The compound of claim 1, wherein A is the group

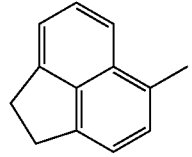 g)

9. The compound of claim 1, wherein A is the group

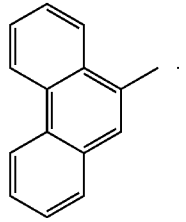 h)

10. The compound of claim 1, wherein A is the group

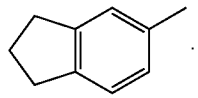 i)

11. The compound of claim 1, wherein A is the group

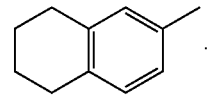 j)

12. The compound of claim 1, wherein A is the group

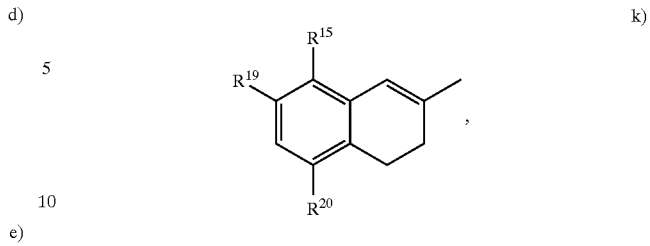 k)

wherein $R^{18}$–$R^{20}$ are each independently selected from hydrogen, lower alkyl or lower alkoxy.

13. The compound of claim 2, selected from:
5-(3-chloro-4-fluoro-phenyl)-3-(2-methyl-imidazol-1-yl-methyl)-pyridazine,
3-(2-methyl-imadazol-1-yl-methyl)-5-(3-trifluormethyl-phenyl)-pyridazine,
5-(3-difluormethyl-4-fluoro-phenyl)-3-(2-methyl-imidazol-1-yl-methyl)-pyridazine,
5-[3-(1,1-difluoro-ethyl)-phenyl]-3-(2-methyl-imidazol-1-yl-methyl)-pyridazine,
5-[3-(1,1-difluoro-ethyl)-4-fluoro-phenyl]-3-(2-methyl-imidazol-1-yl-methyl)-pyridazine,
5-(4-fluoro-3-methyl-phenyl)-3-(2-methyl-imidazol-1-yl-methyl)-pyridazine,
5-(4-chloro-3-methyl-phenyl)-3-(2-methyl-imidazol-1-yl-methyl)-pyridazine,
5-[3-(1,1-difluoro-ethyl)-5-fluoro-phenyl]-3-(2-methyl-imidazol-1-yl-methyl)-pyridazine,
5-(3-difluoromethyl-4-fluoro-phenyl)-3-(2-ethyl-imidazol-1-ylethyl)-pyridazine and
5-(3-cyclopropyl-4-fluoro-phenyl)-3-(2-methyl-imidazol-1-yl-methyl)-pyridazine.

14. The compound of claim 5, which is
5-benzo[b]thiophen-5-yl-3-(2-methyl-imidazol-1-yl-methyl)-pyridazine.

15. The compound of claim 11, which is
5-(3,4-dihydro-naphthalen-2-yl)-3-(2-methyl-imidazol-1-yl-methyl)-pyridazine hydrochloride.

16. A pharmaceutical composition comprising one or more compounds of formula

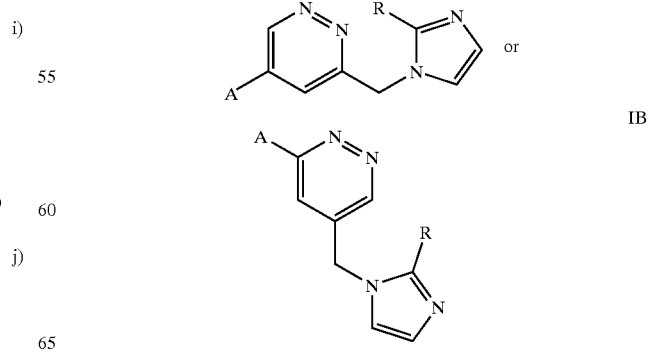

IB wherein
A is selected from:
a) 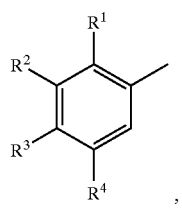
b) 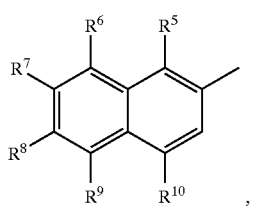
c) 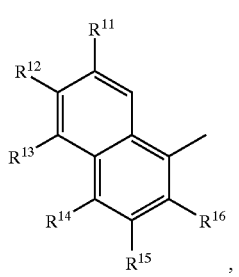
d) 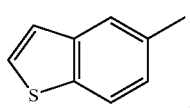
e) 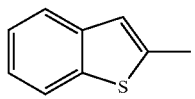
f) 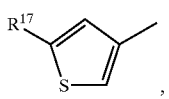
g) 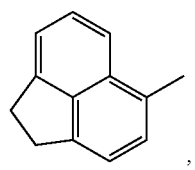
h) 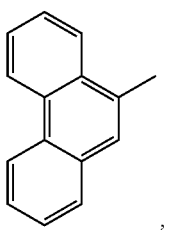
i) 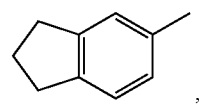
j) 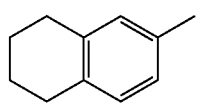 or
k) 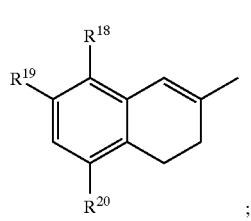;
and
R is hydrogen or lower alkyl;
or a pharmaceutically acceptable salt thereof, and a pharmaceutically acceptable carrier.
17. A method of preparing a compound of formula I, claim 1, comprising:
reacting a compound of formula
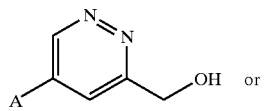 II A
or
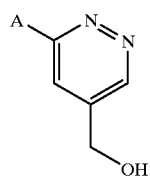 II B
with a compound of formula
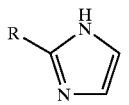 III
to give a compound of formula
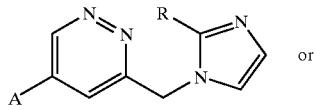 IA
or

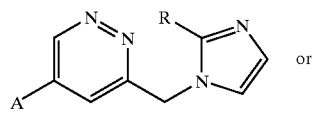
18. A method of preparing a compound of formula I, claim 1, comprising:
reacting a compound of formula
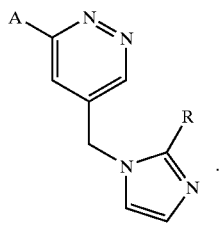
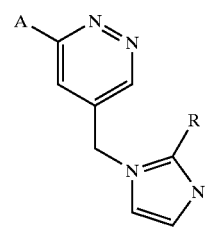
with a compound of formula
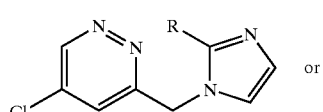
or
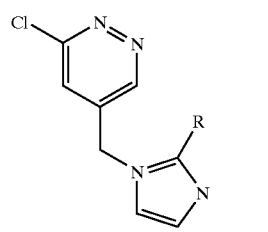
to obtain a compound of formula
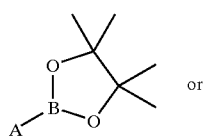
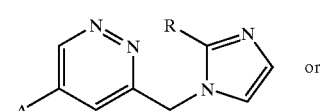
19. A method of treating Alzheimer's disease comprising administering a therapeutically effective amount of a compound of formula
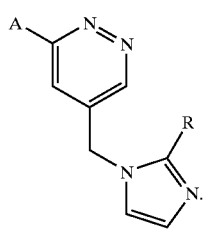
wherein
A is selected from:
a) 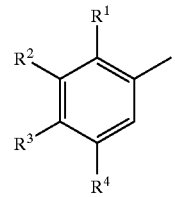
b) 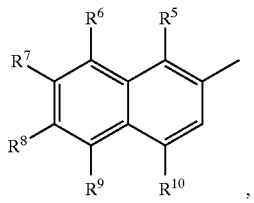
c) 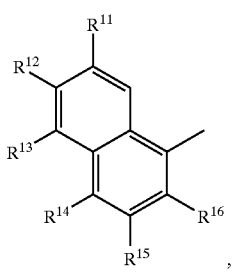
d) 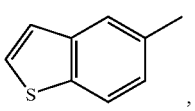
e) 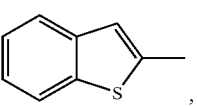
f) 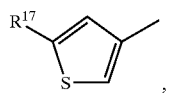

-continued
g) 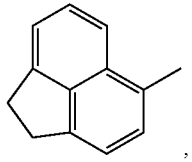
h) 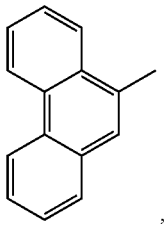
i) 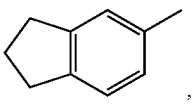
j) 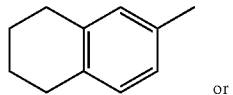 or
k) 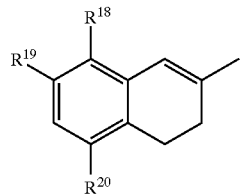
and
R is hydrogen or lower alkyl;
or a pharmaceutically acceptable acid addition salt thereof.
20. A method of treating Parkinson's disease comprising administering a therapeutically effective amount of a compound of formula
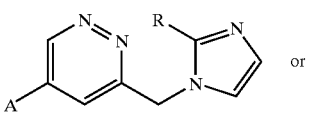 IA
or
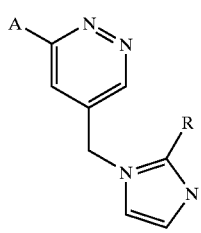 IB
wherein
A is selected from:
a) 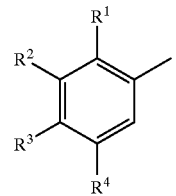
b) 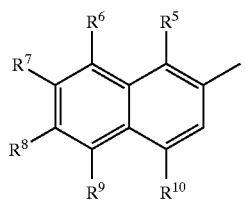
c) 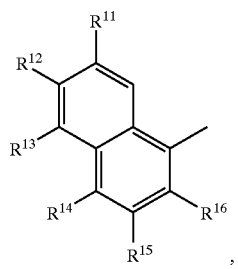
d) 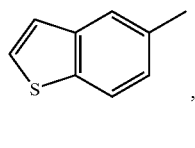
e) 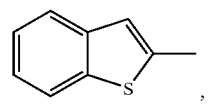
f) 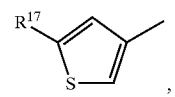
g) 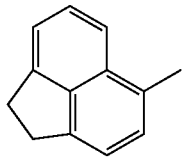
h) 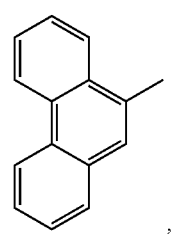

and R is hydrogen or lower alkyl;

or a pharmaceutically acceptable acid addition salt thereof.

21. A method of treating ALS comprising administering a therapeutically effective amount of or compound of formula

IA or

IB wherein

A is selected from:

a)

b)

c)

d)

e)

f)

g)

h)

i)

j)

k)

and R is hydrogen or lower alkyl;

or a pharmaceutically acceptable acid addition salt thereof.

22. A method of treating Huntingdon's disease comprising administering a therapeutically effective amount of a compound of formula
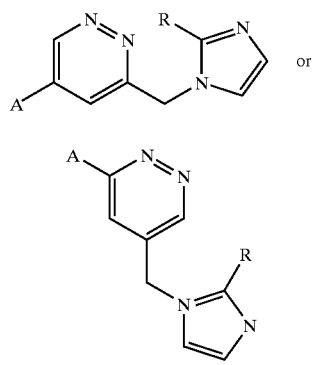
wherein
A is selected from:
a) 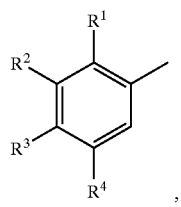,
b) 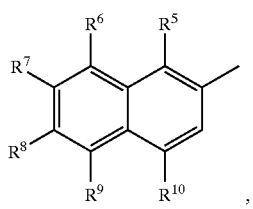,
c) 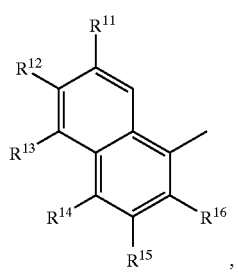,
d)
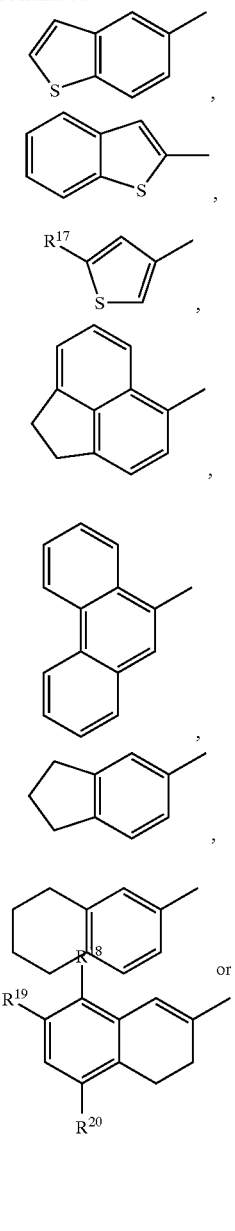
and
R is hydrogen or lower alkyl;
or a pharmaceutically acceptable acid addition salt thereof.
* * * * *

UNITED STATES PATENT AND TRADEMARK OFFICE
CERTIFICATE OF CORRECTION

| | | |
|---|---|---|
| PATENT NO. | : 7,005,432 B2 | Page 1 of 1 |
| APPLICATION NO. | : 10/434955 | |
| DATED | : February 28, 2006 | |
| INVENTOR(S) | : Buettelmann et al. | |

It is certified that error appears in the above-identified patent and that said Letters Patent is hereby corrected as shown below:

TITLE PAGE: Item (73) Col. 1
• The Assignee information reads "Hoffman-La Roche Inc., Nutley, NJ (US)".
The Assignee information should read -- Hoffmann-La Roche Inc., Nutley, NJ (US) --.

IN THE CLAIMS:

• Claim 12, Column 44, lines 1-13, Formula k) reads

" 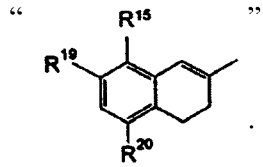 . Formula k) should read -- 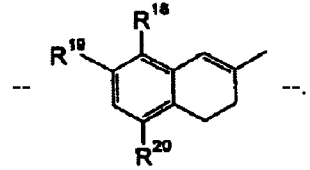 --.

Signed and Sealed this

Tenth Day of October, 2006

JON W. DUDAS
*Director of the United States Patent and Trademark Office*